United States Patent
Su et al.

(10) Patent No.: US 12,090,321 B2
(45) Date of Patent: *Sep. 17, 2024

(54) LEAD PLACEMENT FOR NERVE STIMULATION

(71) Applicant: Medtronic, Inc., Minneapolis, MN (US)

(72) Inventors: Xin Su, Plymouth, MN (US); David A. Dinsmoor, North Oaks, MN (US); Jason E. Agran, Gainesville, FL (US)

(73) Assignee: Medtronic, Inc., Minneapolis, MN (US)

(*) Notice: Subject to any disclaimer, the term of this patent is extended or adjusted under 35 U.S.C. 154(b) by 44 days.

This patent is subject to a terminal disclaimer.

(21) Appl. No.: 17/479,784

(22) Filed: Sep. 20, 2021

(65) Prior Publication Data

US 2022/0001176 A1 Jan. 6, 2022

Related U.S. Application Data

(63) Continuation of application No. 15/958,491, filed on Apr. 20, 2018, now Pat. No. 11,123,555.

(Continued)

(51) Int. Cl.
*A61N 1/36* (2006.01)
*A61B 5/00* (2006.01)
(Continued)

(52) U.S. Cl.
CPC .......... *A61N 1/36007* (2013.01); *A61B 5/065* (2013.01); *A61B 5/296* (2021.01);
(Continued)

(58) Field of Classification Search
CPC .............. A61N 1/36007; A61N 1/0551; A61N 1/36107; A61N 1/36132; A61N 1/36135;
(Continued)

(56) References Cited

U.S. PATENT DOCUMENTS 6,466,817 B1  10/2002  Kaula et al.
7,555,347 B2   6/2009  Loeb
(Continued)

FOREIGN PATENT DOCUMENTS

CN    103842022 A   6/2014
CN    104302354 A   1/2015
(Continued)

OTHER PUBLICATIONS

Communication pursuant to Article 94(3) EPC from counterpart European Application No. 18723225.1, dated Oct. 28, 2021, 4 pp.
(Continued)

*Primary Examiner* — Amanda K Hulbert
*Assistant Examiner* — Natasha Patel
(74) *Attorney, Agent, or Firm* — Shumaker & Sieffert, P.A.

(57) ABSTRACT

Example systems for positioning an implantable electrode may include a stimulation circuitry, a sensing circuitry, and processing circuitry. The stimulation circuitry may generate electrical stimulation deliverable to a patient. The sensing circuitry may sense electromyographic (EMG) responses. The processing circuitry may control the stimulation circuitry to deliver the electrical stimulation at a plurality of different stimulation metric levels at each of a plurality of different positions. The processing circuitry may sense, via the sensing circuitry, electromyographic (EMG) responses to the electrical stimulation. The processing circuitry may score one or more of the different positions for chronic implantation of at least one implantable electrode. The scoring may be based on a stimulation metric level greater than a predetermined metric threshold sufficient to evoke at least some of the sensed EMG responses, and a level of the at least some of the sensed EMG responses.

20 Claims, 10 Drawing Sheets

Related U.S. Application Data

(60) Provisional application No. 62/488,434, filed on Apr. 21, 2017.

(51) Int. Cl.
*A61B 5/06* (2006.01)
*A61B 5/296* (2021.01)
*A61B 5/391* (2021.01)
*A61N 1/05* (2006.01)
*A61N 1/372* (2006.01)

(52) U.S. Cl.
CPC ............. *A61B 5/391* (2021.01); *A61B 5/686* (2013.01); *A61N 1/0551* (2013.01); *A61N 1/36107* (2013.01); *A61N 1/36132* (2013.01); *A61N 1/36135* (2013.01); *A61N 1/36185* (2013.01); *A61N 1/37247* (2013.01); *A61N 1/36021* (2013.01); *A61N 1/36071* (2013.01); *A61N 1/36128* (2013.01)

(58) Field of Classification Search
CPC ............ A61N 1/36185; A61N 1/37247; A61N 1/36021; A61N 1/36071; A61N 1/36128; A61B 5/065; A61B 5/296; A61B 5/391; A61B 5/686

See application file for complete search history.

(56) References Cited

U.S. PATENT DOCUMENTS

| | | | |
|---|---|---|---|
| 7,763,034 B2 | 7/2010 | Siegel et al. | |
| 8,050,769 B2* | 11/2011 | Gharib | A61B 5/389 607/48 |
| 8,412,338 B2 | 4/2013 | Faltys | |
| 8,562,539 B2 | 10/2013 | Marino | |
| 8,626,302 B2 | 1/2014 | Bennett et al. | |
| 8,892,210 B2 | 11/2014 | Fahey | |
| 8,918,184 B1 | 12/2014 | Torgerson et al. | |
| 9,381,356 B2 | 7/2016 | Parker et al. | |
| 9,855,423 B2 | 1/2018 | Jiang et al. | |
| 9,855,431 B2 | 1/2018 | Ternes et al. | |
| 9,872,988 B2 | 1/2018 | Kaula et al. | |
| 10,076,667 B2 | 9/2018 | Kaula et al. | |
| 10,086,203 B2 | 10/2018 | Kaemmerer | |
| 10,092,762 B2 | 10/2018 | Jiang et al. | |
| 10,118,037 B2 | 11/2018 | Kaula et al. | |
| 10,124,171 B2 | 11/2018 | Kaula et al. | |
| 10,238,877 B2 | 3/2019 | Kaula et al. | |
| 10,391,314 B2 | 8/2019 | Hoffer et al. | |
| 10,391,321 B2 | 8/2019 | Kaula et al. | |
| 11,123,555 B2* | 9/2021 | Su | A61N 1/36107 |
| 2007/0265675 A1 | 11/2007 | Lund et al. | |
| 2007/0293782 A1 | 12/2007 | Marino | |
| 2011/0270119 A1 | 11/2011 | Rasmussen | |
| 2012/0191003 A1* | 7/2012 | Garabedian | A61N 1/0551 600/554 |
| 2013/0079841 A1 | 3/2013 | Su et al. | |
| 2013/0204097 A1 | 8/2013 | Rondoni et al. | |
| 2014/0236257 A1 | 8/2014 | Parker et al. | |
| 2016/0045747 A1* | 2/2016 | Jiang | A61N 1/0504 607/40 |
| 2016/0045751 A1 | 2/2016 | Jiang et al. | |
| 2016/0136443 A1* | 5/2016 | Grandhe | A61N 1/36071 607/60 |
| 2016/0144194 A1* | 5/2016 | Roothans | A61N 1/0534 607/45 |
| 2018/0110987 A1 | 4/2018 | Parker | |
| 2018/0132760 A1 | 5/2018 | Parker | |
| 2018/0228547 A1 | 8/2018 | Parker et al. | |
| 2018/0304075 A1 | 10/2018 | Su et al. | |

FOREIGN PATENT DOCUMENTS

| | | |
|---|---|---|
| CN | 105916549 A | 8/2016 |
| CN | 106232176 A | 12/2016 |
| EP | 3180072 B1 | 11/2018 |
| EP | 2870979 B1 | 2/2021 |
| WO | 2019204884 A1 | 10/2019 |

OTHER PUBLICATIONS

Pizarro-Berdichevsky et al., "Motor Response Matters: Optimizing Lead Placement Improves Sacral Neuromodulation Outcomes," The Journal of Urology, Nov. 14, 2017, 11 pp.

Noblett et al., "Neuromodulation and the Role of Electrodiagnostic Techniques," International Urogynecology Journal, vol. 21, Supp 2, Dec. 2010, pp. S461-S466.

Matzel et al., "Sacral Neuromodulation: Standardized Electrode Placement Technique," Neuromodulation: Technology at the Neural Interface, Oct. 4, 2017, 9 pp.

Mclennan et al., "The Role of Electrodiagnostic Techniques in the Reprogramming of Patients with a Delayed Suboptimal Response to Sacral Nerve Stimulation," International Urogynecology Journal, vol. 14, Mar. 12, 2003, pp. 98-103.

Noblett et al., "Implantable Neurostimulator Programming at Implant and Follow-up in a Large Prospective Trial of Sacral Neuromodulation Therapy for Overactive Bladder Patients," Female Pelvic Medicine and Reconstructive Surgery, vol. 20, No. 4, Jul./Aug. 2014, pp. S367-S368.

International Preliminary Report on Patentability from International Application No. PCT/US2018/028626, mailed Oct. 31, 2019, 8 pp.

International Search Report and Written Opinion of International Application No. PCT/US2018/028626, mailed Jul. 4, 2018, 14 pp.

Prosecution History from U.S. Appl. No. 15/958,491, dated Aug. 6, 2020 through May 3, 2021, 61pp.

Response to Examination Report dated Oct. 28, 2021, from counterpart European Application No. 18723225.1, filed Feb. 21, 2021, 4 pp.

Office Action, and translation thereof, from counterpart Chinese Application No. 201880016539.2 dated Mar. 13, 2023, 17 pp.

Second Office Action, and translation thereof, from counterpart Chinese Application No. 201880016539.2 dated Sep. 19, 2023, 30 pp.

Third Office Action and Search Report, and translation thereof, from counterpart Chinese Application No. 201880016539.2 dated Jan. 29, 2024, 18 pp.

Communication pursuant to Article 94(3) EPC from counterpart European Application No. 18723225.1 dated Jul. 9, 2024, 6 pp.

\* cited by examiner

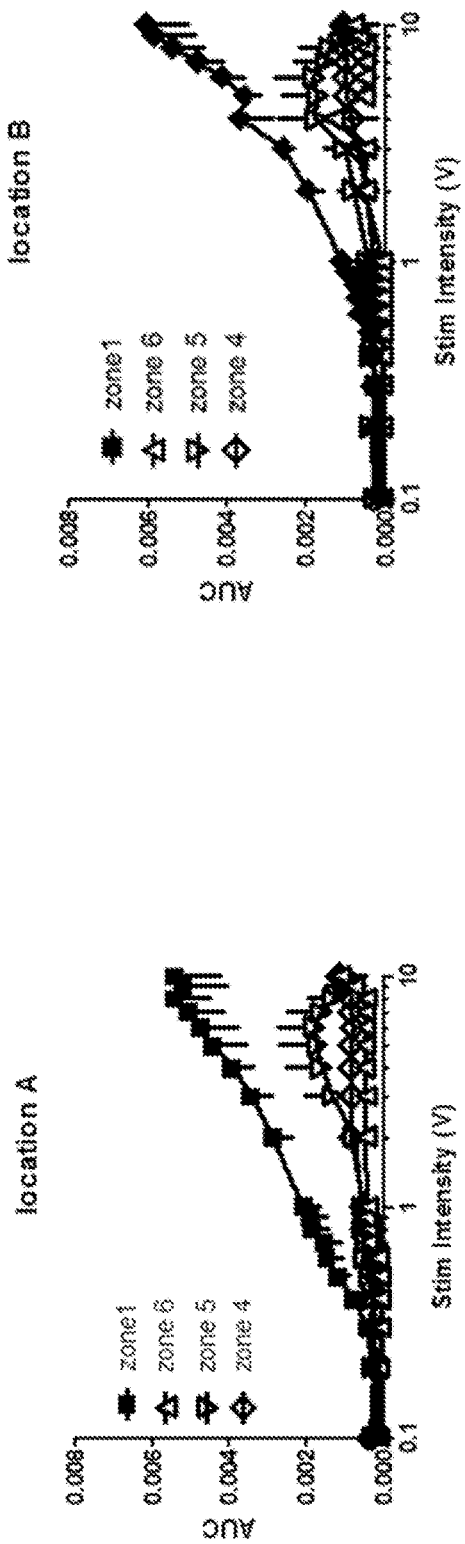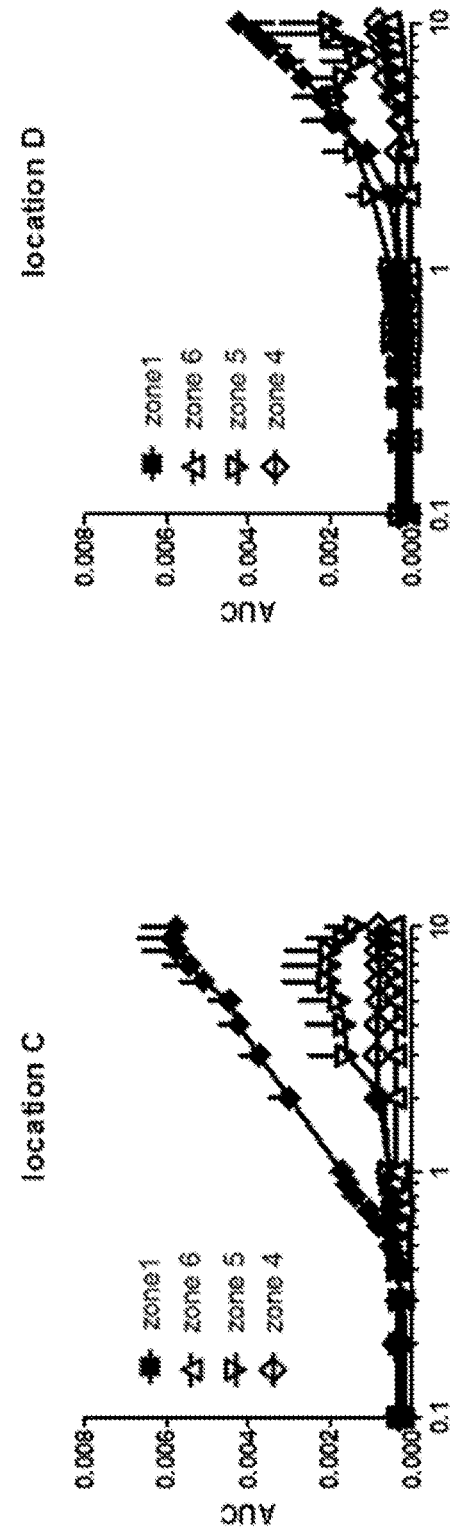

LEAD PLACEMENT FOR NERVE STIMULATION

This application is a continuation of U.S. patent application Ser. No. 15/958,491, filed Apr. 20, 2018, which claims the benefit of, and priority to, U.S. Provisional Patent Application Ser. No. 62/488,434, filed on Apr. 21, 2017, the entire content of application Ser. No. 15/958,491 and 62/488,434 are incorporated by reference herein.

TECHNICAL FIELD

The disclosure relates to placement of medical leads and, more particularly, placement of leads for electrical stimulation.

BACKGROUND

Electrical stimulation systems may be used to deliver electrical stimulation therapy to patients to treat a variety of patient symptoms or conditions, for example, conditions related to the central or the peripheral nervous systems, or pelvic floor disorders. Pelvic floor disorders may include urinary incontinence (e.g., stress incontinence or urge incontinence), fecal incontinence, pelvic pain, bowel dysfunction, and sexual dysfunction. Some electrical stimulation systems may include one or more electrodes to provide electrical stimulation at or within a tissue of a patient.

SUMMARY

In some examples, the disclosure describes an example system that includes stimulation circuitry, sensing circuitry, and processing circuitry. The stimulation circuitry may be configured to generate electrical stimulation deliverable to a patient. The sensing circuitry may be configured to sense electromyographic (EMG) responses from the patient. The processing circuitry may be configured to control the stimulation circuitry to deliver, via at least one electrode, the electrical stimulation at a plurality of different stimulation metric levels at each of a plurality of different positions within the patient. The processing circuitry may be configured to sense, via the sensing circuitry, electromyographic (EMG) responses from the patient to the electrical stimulation. The processing circuitry may be configured to score one or more of the different positions for chronic implantation of at least one implantable electrode. The processing circuitry may perform the scoring based on at least one stimulation metric level of the plurality of different stimulation metric levels greater than a predetermined metric threshold sufficient to evoke at least some of the sensed EMG responses to the delivery of the electrical stimulation at a respective position of the one or more positions, and a level of the at least some of the sensed EMG responses produced in response to the delivery of the electrical stimulation at the at least one stimulation metric level at the respective position.

In some examples, the disclosure describes an example technique for positioning at least one electrode. The example technique may include delivering electrical stimulation at a plurality of different stimulation metric levels at each of a plurality of different positions within a patient. The example technique may include sensing electromyographic (EMG) responses from the patient to the electrical stimulation. The example technique may include scoring one or more of the different positions for chronic implantation of at least one implantable electrode. The scoring may be based on at least one stimulation metric level of the plurality of different stimulation metric levels greater than a predetermined metric threshold sufficient to evoke at least some of the sensed EMG responses to the delivery of the electrical stimulation at a respective position of the one or more different positions, and a level of the at least some of the sensed EMG responses produced in response to the delivery of the electrical stimulation at the at least one stimulation metric level at the respective position.

In some examples, the disclosure describes an example non-transitory computer readable storage medium including instructions that, when executed, cause processing circuitry to deliver electrical stimulation at a plurality of different stimulation metric levels at each of a plurality of different positions a patient. The instructions, when executed, may cause processing circuitry to sense electromyographic (EMG) responses from the patient to the electrical stimulation. In instructions, when executed, may cause processing circuitry to score one or more of the different positions for chronic implantation of at least one implantable electrode. The scoring may be based on at least one stimulation metric level of the plurality of different stimulation metric levels greater than a predetermined metric threshold sufficient to evoke at least some of the sensed EMG responses to the delivery of the electrical stimulation at a respective position of the one or more positions, and a level of the at least some of the sensed EMG responses produced in response to the delivery of the at least one electrical stimulation at the at least one stimulation metric level at the respective position.

The details of one or more examples are set forth in the accompanying drawings and the description below. Other features, objects, and advantages will be apparent from the description and drawings, and from the claims.

BRIEF DESCRIPTION OF DRAWINGS

FIGS. 11A-11D are charts illustrating example variations in EMG signals sensed at different zones and locations with different stimulation intensities.

DETAILED DESCRIPTION

Figure 1:
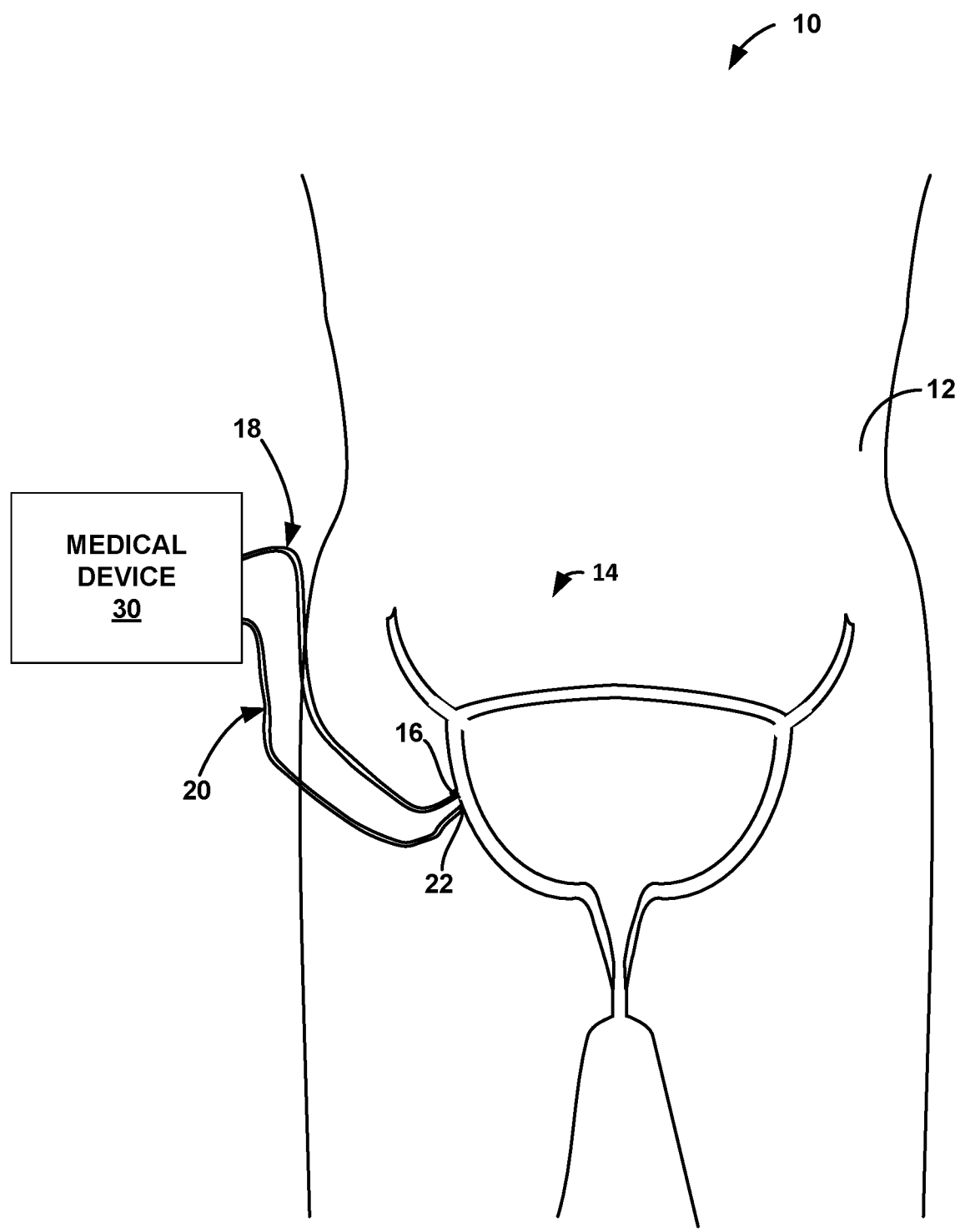
FIG. 1 is a conceptual and schematic diagram illustrating an example electrical stimulation system that is configured to provide electrical stimulation to a tissue of a patient.

The disclosure describes example systems and techniques for positioning and placing implantable electrodes for neurological stimulation. Clinicians, such as physicians or other medical technicians, may place implantable electrodes within or at a tissue of a patient to provide stimulation to target sites, e.g., at or near nerves, to treat patient conditions or symptoms. Clinicians may seek locating appropriate positions, orientations, or configurations of one or electrodes to provide an appropriate level of stimulation to the target sites, without, for example, substantially impacting other sites. Electromyogram (EMG) responses evoked by the electrical stimulation delivered by one or more electrodes as the positions, orientations, or configurations of electrodes are changed may be used to guide electrode placement.

For example, the EMG responses to different stimulation metric levels delivered by electrodes in different positions, orientations, or configurations may be monitored, and an electrode position, orientation, or configuration associated with a sufficiently high EMG response at or adjacent a target site in response to a relatively low stimulation metric level may be scored and/or selected for chronic implantation of one or more electrodes. The sufficiently high EMG response may be indicative of delivery of the stimulation to the intended target site that exceeds a certain threshold, such as an activation threshold or motor threshold, representative of stimulation that affects desired tissue (e.g., a targeted nerve and/or muscle). In some examples, a sufficiently high EMG response may be sought at a target site, while a relatively low EMG response may be sought at a different site, for example, at a site at which no stimulation is intended. In some examples, EMG responses of a number of sites adjacent to or remote from the target site may be monitored, and electrode placement may be guided by sufficiently high EMG responses adjacent the target site, and sufficiently low EMG responses remote from the target site. In other words, EMG response may be analyzed for multiple positions and compared to determine an appropriate position for delivering stimulation therapy that provides desired therapy while reducing undesirable side effects.

In some examples, the electrodes used to sense EMG responses may be or include the implantable electrodes to be chronically implanted within the patient. In other examples, temporary electrodes may be used to evaluate different electrode placements in a test phase, and after suitable placement locations are identified or selected, a different set of one or more implantable electrodes may be implanted at the selected position or positions for chronic delivery of stimulation. The selected position may be based on scores assigned to each position of the one or more of the different positions for chronic implantation of at least one implantable electrode. The scores may be based on at least one stimulation metric level of the plurality of different stimulation metric levels greater than a predetermined metric threshold sufficient to evoke at least some of the sensed EMG responses to the delivery of the electrical stimulation at a respective position of the one or more positions. The scores may also be based on a level of the at least some of the sensed EMG responses produced in response to the delivery of the electrical stimulation at the at least one stimulation metric level at the respective position.

Using EMG-guided electrode placement may reduce fluoroscopy and/or X-ray usage, decrease procedure time, and provide an objective tool for selecting appropriate electrode location based on EMG response thresholds to targeted stimulation. The accuracy of chronic electrode placement thus may be increased, which may enhance therapy efficacy outcomes and resultant patient quality of life.

Example systems and techniques according to the disclosure may be used to guide electrode placement at tissue sites associated with any predetermined stimulation target, for example, peripheral and central nervous systems, or for any suitable neuromodulation stimulation areas.

An example system may include at least one electrode and a medical device. The medical device, for example, a controller or a programmer, may be configured to control the at least one electrode to deliver electrical stimulation at a plurality of different stimulation metric levels at each of a plurality of different positions within a patient. The medical device may sense electromyographic (EMG) responses from the patient to the electrical stimulation, and score one or more of the different positions for chronic implantation of at least one implantable electrode. The scoring may be based on at least one stimulation metric level of the plurality of different stimulation metric levels greater than a predetermined metric threshold sufficient to evoke at least some of the sensed EMG responses to the delivery of the electrical stimulation at a respective position of the one or more positions, and a level of the at least some of the sensed EMG responses produced in response to the delivery of the electrical stimulation at the at least one stimulation metric level at the respective position.

An example technique for positioning at least one electrode may include delivering electrical stimulation at a plurality of different stimulation metric levels at each of a plurality of different positions within a patient. The technique may further include sensing electromyographic (EMG) responses from the patient to the electrical stimulation. The technique may further include scoring, based on the sensed EMG responses, one or more of the positions for chronic implantation of at least one implantable electrode. In some examples, a position may be scored based on the electrode position at which stimulation produces the strongest EMG response combined with a low stimulation metric needed to trigger the EMG response, for example, in comparison to other adjacent locations, and accounting for absence of undesirable side effects. In some examples, a medical device may process the EMG response to guide positioning of the at least one electrode.

For example, after initially placing an electrode at an initial site, the medical device would begin recording EMG responses to sequential electrical stimulation. If electrode advancement or movement (which may be controlled, for example, by a clinician, or driven by a lead or electrode placement motor), results in an increased EMG response, the medical device may decrease the stimulation metric level until both the lead electrical field is mapped and initial stimulation parameters are achieved. The electrode placement could further be fine-tuned, for example, using micromovements along different directions, after initial selection of a site. The final placement for chronic implantation of one or more electrodes may be chosen based on the strongest EMG response combined with at least one stimulation metric level sufficient to evoke the EMG responses, in comparison to adjacent locations, for example, at least three locations. Undesirable side effects, for example, stimulation at unintended sites that may cause patient discomfort or unintended functionality may additionally be monitored and used to guide the electrode placement. Example systems may thus provide feedback to the clinician in the form of one or more visual, audio, haptic, or other signals or via a display or as the clinician moves one or more electrodes (e.g., real time or near real time feedback) to guide electrode placement. Thus, a clinician can navigate electrodes to a position to deliver stimulation to one or more intended target sites in a guided, semi-automated, or substantially automated manner.

FIG. 1 is a conceptual and schematic diagram illustrating an example electrical stimulation system 10 that is configured to provide electrical stimulation to a tissue of a patient 12. In some examples, the tissue may include the nervous system, for example the peripheral or central nervous system. In some examples, the tissue may be within a pelvic floor 14 of patient 12. System 10 may deliver electrical stimulation to a target site within the tissue, for example, a site adjacent or at a nerve of patient 12. The nerve can be a nerve that influences the behavior of pelvic floor muscles of patient 12, such as a sacral nerve, a pudendal nerve or a branch of the sacral or pudendal nerves. While the sacral and pudendal nerves are primarily referred to throughout the disclosure, in other examples, therapy system 10, as well as the other systems and methods for training and strengthening a pelvic floor nerve can include delivery of stimulation to tissue sites proximate other nerves in addition to or instead of the sacral or pudendal nerves. Moreover, reference to the sacral and pudendal nerves may include branches of the sacral and pudendal nerves that may also influence the behavior of pelvic floor muscles of patient 12. In general, the sacral nerves include five sacral nerves that emerge from the sacrum. In some examples, the sacral vertebrae (S1-S5) may be used to number the sacral nerves. The sacral nerves contribute to the sacral plexus (a network of intersecting nerves that innervates the posterior thigh, part of the lower leg, the foot, and part of the pelvis) and the coccygeal plexus (a network of intersecting nerves near the coccyx bone, e.g., the tailbone, that innervates the skin of the coccyx bone and around the anus). In general, the pudendal nerve is a somatic nerve in the pelvic region, which is a large branch of the sacral plexus. The pudendal nerve innervates the external genitalia, the urinary sphincters, and the anal sphincters.

Electrical stimulation system 10 includes at least one electrode. The at least one electrode may include at least one stimulation electrode 16 coupled to a stimulation lead 18, for example, as shown in FIG. 1. In addition, the at least one electrode may include at least one sensing electrode 22 coupled to a sensing lead 20 for sensing EMG responses generated in response to stimulation delivered via stimulation lead 18 or stimulation electrode 16. In alternative examples, each electrode 16 and 22 (and other electrodes) may support both delivery of stimulation signals and sensing physiological signals and/or a single lead may include both stimulation and sensing electrodes. Electrical stimulation system 10 also includes a medical device 30 for controlling stimulation electrode 16 and for receiving and analyzing signals received from sensing electrode 22. Medical device 30 controls delivery of electrical stimulation therapy to target tissue site 14 located proximate a nerve of patient 12 by generating a programmable electrical stimulation signal (e.g., in the form of electrical pulses) and delivering the electrical stimulation signal to target tissue site 14 via stimulation lead 18. In some examples, stimulation lead 18 includes one or more stimulation electrodes, for example, stimulation electrode 16. In some examples, stimulation electrode 16 may include a plurality of stimulation electrodes 60a-60d, disposed at a distal end 18b of stimulation lead 18 (FIG. 2).

Figure 2:
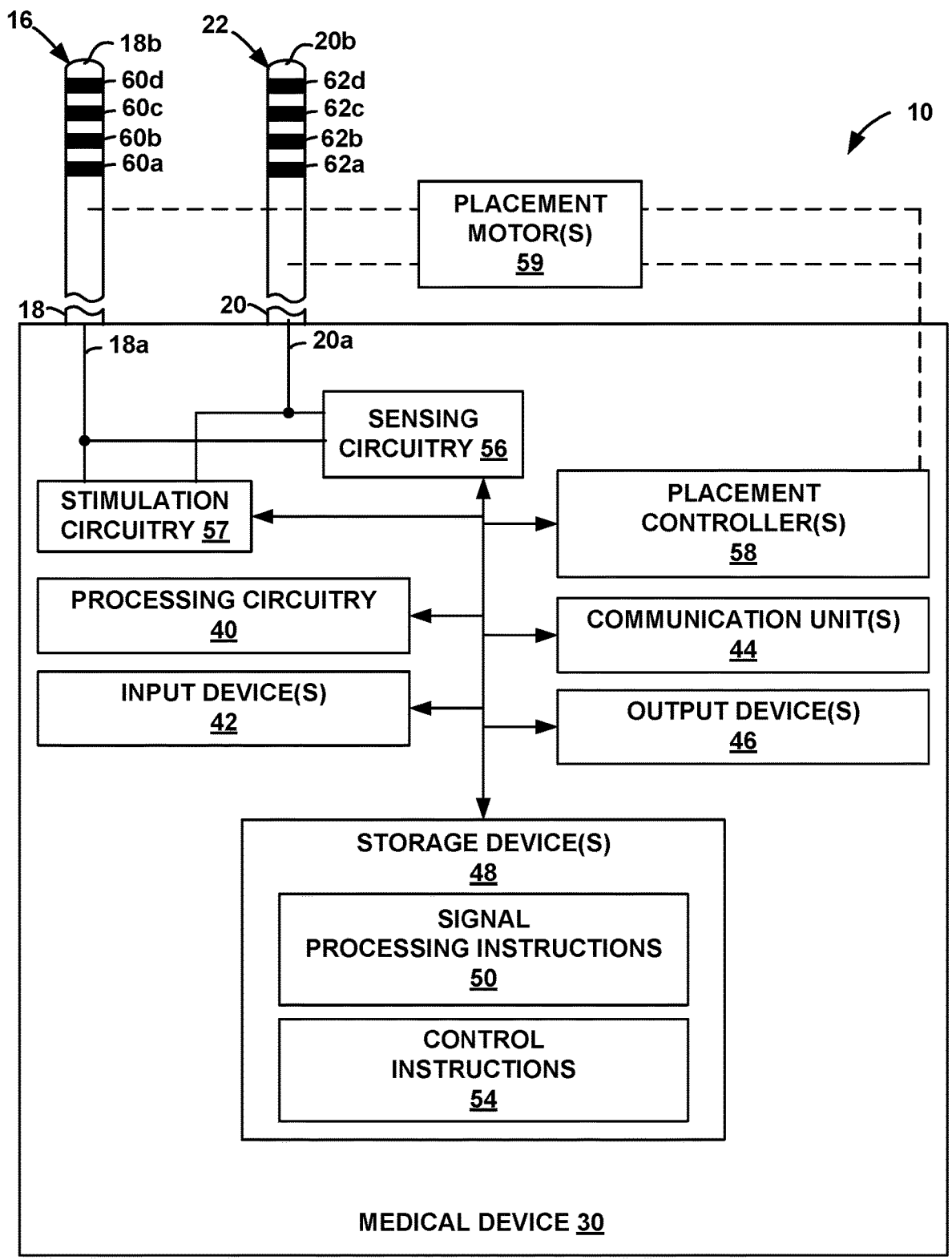
FIG. 2 is a block diagram illustrating components of an example medical device coupled to at least one stimulation electrode.

FIG. 2 is a block diagram illustrating components of medical device 30 coupled to at least one stimulation electrode 16. In some examples, stimulation lead 18 includes a lead body, and proximal end 18B of stimulation lead 18 may be electrically coupled to medical device 30 via one or more conductors extending substantially through the lead body between the one or more stimulation electrodes carried by stimulation lead 18 and medical device 30. Thus, stimulation electrode 16 may be implanted proximate to target tissue site 14 such that the electrical stimulation is delivered from medical device 30 to target tissue site 14 via stimulation electrode 16. In some examples, stimulation lead 18 may also carry at least one sensing electrode via which medical device 30 can sense one or more physiological parameters (e.g., nerve signals, EMG, and the like) of patient 12, in addition to the at least one stimulation electrode 16 carried by stimulation lead 18. In some examples, system 10 may include, instead of or in addition to sensing electrodes carried by stimulation lead 18, separate sensing electrode 22 coupled to sensing lead 20 separate from stimulation lead 18, as shown in FIGS. 1 and 2. Thus, in some examples, medical device 30 may be coupled to at least one sensing electrode 22 via sensing lead 20. In other examples, medical device 30 may be coupled to at least one electrode via at least one lead, which may include one or both at least one stimulation electrode 16 and sensing electrode 22. In some examples, the at least one electrode may function as at least one stimulation electrode 16 at one instance of time and as sensing electrode 22 at another instance of time.

In the examples shown in FIGS. 1 and 2, stimulation lead 18 and sensing lead 20 are cylindrical. However, in other examples, one or both of stimulation lead 18 and sensing lead 20 may have any suitable shape or geometry, including one or more of flat, braided, or coiled portions along their respective lengths, and having any suitable cross-section, including circular, oval, or polygonal. At least one stimulation electrode 16 of stimulation lead 18 (e.g., stimulation electrodes 60 illustrated in FIG. 2), or at least one sensing electrode 22 (e.g., sensing electrodes 62 illustrated in FIG. 2) of sensing lead 20, may be ring electrodes, segmented electrodes, or partial ring electrodes. Segmented and partial ring electrodes each extend along an arc less than 360 degrees (e.g., 90-120 degrees) around the outer perimeter of stimulation lead 18 or of sensing lead 20 respectively. In some examples, segmented electrodes may be useful for targeting different fibers of the same or different nerves to generate different physiological effects or for delivering relatively high frequency stimulation (e.g., about 66 Hertz) and relatively low frequency stimulation (e.g., about 15 Hertz) to activate both fast twitch muscles and slow twitch muscles substantially simultaneously or at alternating time slots. In some examples, stimulation lead 18 or sensing lead 20 may be, at least in part, paddle-shaped (i.e., a "paddle" lead).

In some examples, at least one stimulation electrode 16 of stimulation lead 18 or at least one sensing electrode 22 of sensing lead 20 may be cuff electrodes that are configured to extend at least partially around a nerve (e.g., extend axially around an outer surface of a nerve). In some cases, delivering stimulation via one or more cuff electrodes and/or segmented electrodes may help achieve a more uniform electrical field or activation field distribution relative to the nerve in some examples, which may help minimize discomfort to patient 12 that results from the delivery of electrical stimulation. An electrical field represents the areas of a patient anatomical region that are covered by an electrical field during delivery of electrical stimulation to tissue within patient 12. The electrical field may define the volume of tissue that is affected when at least one stimulation electrode 16 of stimulation lead 18 is activated. An activation field represents the neurons that will be activated by the electrical field in the neural tissue proximate to the activated electrodes.

In some examples, at least one sensing electrode 22 may include one or more of at least one stimulation electrode 16, other implanted electrodes, external patch electrodes, or needle electrodes. In some examples, at least one sensing electrode 22 may include one or both of at least one local sensing electrode substantially adjacent the respective position of the different positions or at least one remote sensing electrode substantially remote from the respective position of the different positions.

The illustrated numbers and configurations of stimulation lead 18, at least one stimulation electrode 16, sensing lead 20, and at least one sensing electrode 22 carried by sensing lead 20 are merely examples. Different configurations, e.g., different quantities and/or positions of leads and electrodes, are possible. For example, in other examples, medical device 30 may be coupled to additional leads or lead segments having one or more electrodes positioned at different locations in the target stimulation region of patient 12, for example, as described with reference to FIG. 3. Thus, medical device 30 may control the placement of electrodes, or may guide the placement of electrodes by a clinician, as described with reference to example techniques described elsewhere in the disclosure.

In some examples, medical device 30 may include, for example, a desktop computer, a laptop computer, a workstation, a server, a mainframe, a cloud computing system, or the like. In some examples, medical device 30 may include one or both of a programmer or a controller, for example, a patient-controlled or clinician-controlled programmer. In some examples, medical device 30 may include an implantable medical device (IMD).

In the example illustrated in FIG. 2, medical device 30 includes processing circuitry 40, one or more input devices 42, one or more communication units 44, one or more output devices 46, and one or more storage devices 48. In some examples, one or more storage devices 48 stores signal processing instructions 50, and control instructions 54. Medical device 30 may also include one or both of sensing circuitry 56 and stimulation circuitry 57. In some examples, one or both of sensing circuitry 56 and stimulation circuitry 57 may be coupled to one or both of stimulation electrode 16 via stimulation lead 18 and sensing electrode 22 via sensing lead 20, as shown in FIG. 2. In other examples, medical device 30 may include additional components or fewer components than those illustrated in FIG. 2.

Processing circuitry 40 is configured to implement functionality and/or process instructions for execution within medical device 30. For example, processing circuitry 40 may be capable of processing instructions stored by storage device 48. Examples of processing circuitry 40 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 48 may be configured to store information within medical device 30 during operation. Storage devices 48, in some examples, include a computer-readable storage medium or computer-readable storage device, for example, a non-transitory computer-readable storage medium. In some examples, storage devices 48 include a temporary memory, meaning that a primary purpose of storage device 48 is not long-term storage. Storage devices 48, in some examples, include a volatile memory, meaning that storage device 48 does not maintain stored contents when power is not provided to storage device 48. Examples of volatile memories include random access memories (RAM), dynamic random access memories (DRAM), static random access memories (SRAM), and other forms of volatile memories known in the art. In some examples, storage devices 48 are used to store program instructions for execution by processing circuitry 40. Storage devices 48, in some examples, are used by software or applications running on medical device 30 to temporarily store information during program execution.

In some examples, storage devices 48 may further include one or more storage device 48 configured for longer-term storage of information. In some examples, storage devices 48 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Medical device 30 may further include one or more communication units 44. Medical device 30 may utilize communication units 44 to communicate with external devices (for example, a programmer, a controller, or one or both of at least one stimulation electrode 16 and at least one sensing electrode 22) via one or more networks, such as one or more wired or wireless networks. Communication unit 44 may include a network interface card, such as an Ethernet card, an optical transceiver, a radio frequency transceiver, or any other type of device that can send and receive information. Other examples of such network interfaces may include WiFi radios or Universal Serial Bus (USB). In some examples, medical device 30 utilizes communication units 44 to wirelessly communicate with an external device such as a server.

Medical device 30 also includes one or more input devices 42. Input devices 42, in some examples, are configured to receive input from a user through tactile, audio, or video sources. Examples of input devices 42 include a mouse, a keyboard, a voice responsive system, video camera, microphone, touchscreen, a control panel including one or more switches, knobs, or potentiometers, or any other type of device for detecting a command from a user.

Medical device 30 may further include one or more output devices 46. Output devices 46, in some examples, are configured to provide output to a user using audio or video media. For example, output devices 46 may include a display, a sound card, a video graphics adapter card, or any other type of device for converting an output signal into an appropriate form understandable to humans or machines. In some examples, output device 46 may include a fluoroscopic display configured to indicate respective positions of at least one implantable electrode or at least one stimulation electrode 16, and the respective EMG responses associated with the at least one implantable electrode or at least one stimulation electrode 16. In some examples, output device 46 is configured to present scores of one or more of the at least one electrode or the at least one implantable electrode and the respective EMG responses associated with the at least one electrode or the at least one implantable electrode. In some examples, medical device 30 outputs a representation of a suggested electrode movement direction, for example, as described with reference to FIG. 4A elsewhere in the disclosure.

In some examples, medical device 30 may generate an alert indicative of one or more of EMG responses, stimulation intensities, or electrode placement position, direction, or configuration, via output devices 46. For example, medical device 30 may generate auditory signals, such as a beep, an alert tone, or an alerting sound, or visual signals, such as an icon on a display, flashing lights, or a combination of visual and audible signals, to indicate a level of an EMG response or a stimulation metric level (for example, a stimulation intensity, frequency, pulse width, or some combination thereof), or an electrode placement configuration or position. As another example, medical device 30 may generate an alert that is transmitted over a network to another medical device, including a hand-held medical device, for instance, a cellphone.

In some examples, medical device 30 may be configured to control output device 46 to output a real-time or near real-time feedback signal to guide a clinician on one or both of moving an electrode on a movable lead or locating an electrode along an axial length of a fixed lead. For example, the signal may guide the clinician on moving stimulation electrode 16 on movable stimulation lead 18 or sensing electrode 22 on movable sensing lead 20, or locating stimulation electrode 16 along an axial length of fixed stimulation lead 18 or sensing electrode 22 along an axial length of fixed sensing lead 20. In some examples, the feedback signal may include one or more of an electronic, visual, audible, or haptic signal.

Medical device 30 also may include signal processing instructions 50 and control instructions 54. In some examples, processing circuitry 40 pre-processes or processes at least one data signal indicative of an EMG response, for example, a signal received from at least one sensing electrode, to prepare the least one data signal for analysis, according to signal processing instructions 50. Processing circuitry 40 may analyze at the least one data signal according to signal processing instructions 50 to determine a magnitude of an EMG response. Functions performed by processing circuitry 40 according to signal processing instructions 50 and control instructions 54 are explained below with reference to the example flow diagram illustrated in FIG. 5.

Signal processing instructions 50 and control instructions 54 may be implemented in various ways. For example, signal processing instructions 50 and/or control instructions 54 may be implemented as software, such as an executable application or an operating system, or firmware executed by processing circuitry 40. In other examples, signal processing instructions 50 and/or control instructions 54 may be implemented as part of a hardware unit of medical device 30.

In some examples, system 10 may include at least on placement motor 59, as shown in FIG. 2. At least one placement motor 59 may be coupled or one or both of stimulation lead 18 or sensing lead 20, to respectively control movement of stimulation electrode 16 or sensing electrode 22. Placement motor 59 may include any suitable mechanism, for example, at least one motor, at least one servomotor, at least one displacement mechanism, for example, an electromagnetic rail or piston, or any mechanism that can be used to control a position of stimulation lead 18 or sensing lead 20. In some examples, medical device 30 may include at least one placement controller 58 for controlling placement motor 59. For example, medical device 30 may send a signal to placement motor 59 via placement controller 58 for controlling a position of stimulation lead 18 or sensing lead 20. In some examples, medical device 30 may receive a signal from placement motor 59 via placement controller 58 that may be indicative of a position of stimulation lead 18 or sensing lead 20. For example, placement motor 59 may include a sensor to sense the position of stimulation lead 18 or sensing lead 20. Thus, in some examples, medical device 30 may be configured to control placement motor 59 to move one or both of at least one stimulation electrode 16 or at least one sensing electrode 22 toward a selected position of the one or more positions.

Medical device 30 may include additional components that, for clarity, are not shown in FIG. 2. For example, medical device 30 may include a power supply to provide power to the components of medical device 30. Similarly, the components of medical device 30 shown in FIG. 2 may not be necessary in every example of medical device 30.

Figure 3:
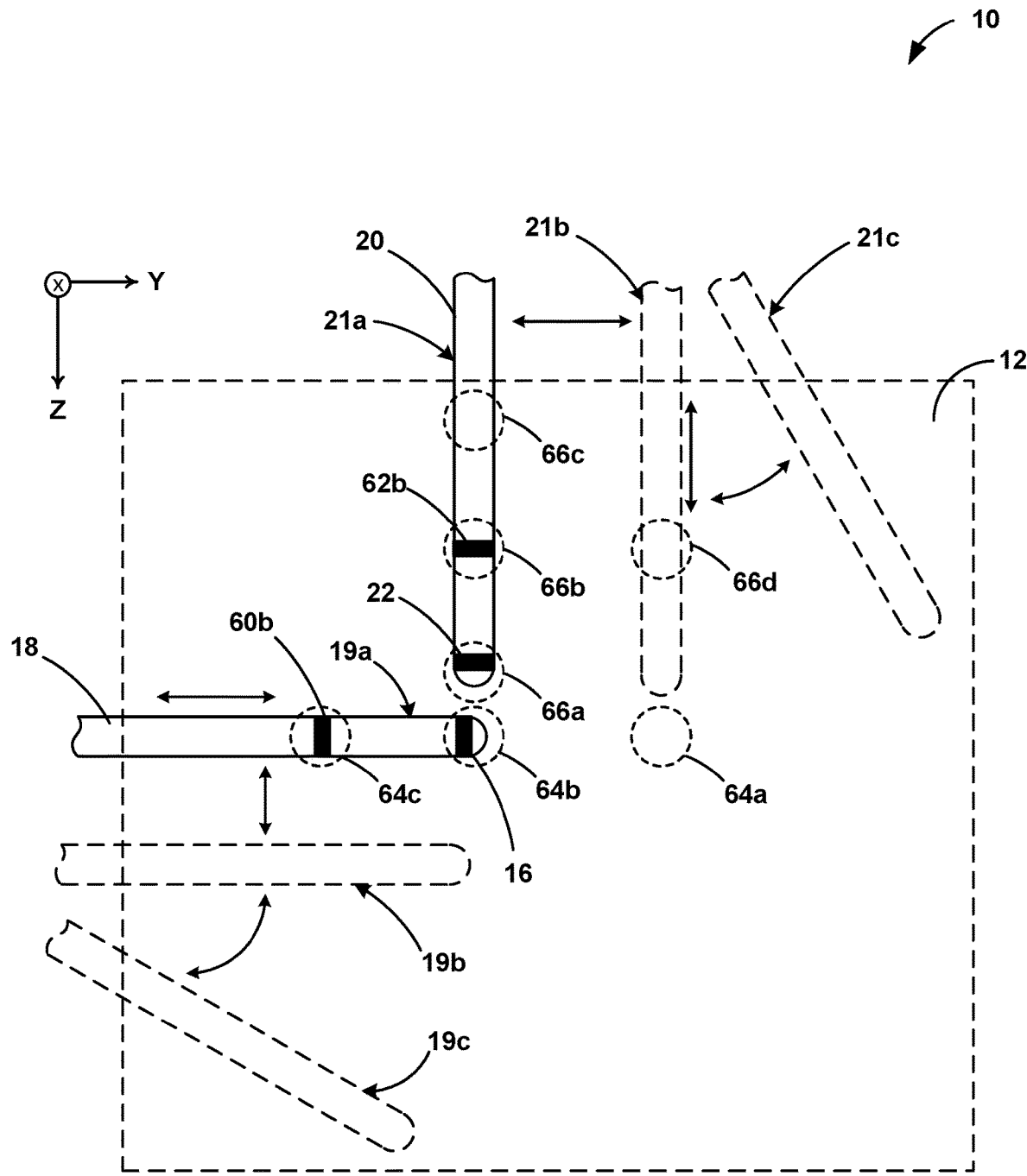
FIG. 3 is a conceptual and schematic diagram illustrating example different configurations of at least one stimulation lead and at least one sensing lead at a tissue of a patient.

FIG. 3 is a conceptual and schematic diagram illustrating example different configurations of at least one stimulation lead 18 and at least one sensing lead 20 at a tissue of patient 12. Medical device 30 may control the placement of electrodes, or provide guidance to a clinician for placement of electrodes, for example, different electrode configurations described with reference to FIG. 3. One or both of stimulation lead 18 and sensing lead 20 can be moved along a predetermined direction, for example, along one of X, Y, or Z axis shown in FIG. 3, or along any three-dimensional line, or within any plane, or in any arbitrary three-dimensional direction. In some examples, the predetermined direction may result in a forward, backward, upward, downward, or sideways movement, or in an inclined, tilted, or canted movement of stimulation lead 18 or sensing lead 20. For example, one or both of stimulation lead 18 or sensing lead 20 may be moved, relative to an initial position, forward, backward, upward, downward, or sideways, or may be tilted or inclined, or may be rotated along any suitable axis, resulting in configurations such as 19a-19c of stimulation lead 19, or 21a-21c of sensing lead 20, shown in FIG. 3.

In some examples, moving stimulation lead 18 results in a relative motion between stimulation electrode 16 and a target stimulation site, for example, one or more of stimulation sties 64a, 64b, and 64c (collectively "stimulation sites 64") shown in FIG. 3. In some examples, moving sensing lead 18 results in a relative motion between sensing electrode 22 and a target sensing site, for example, one or more of stimulation sites 66a, 66b, and 66c (collectively "stimulation sites 66") shown in FIG. 3. In some examples, one or more of sensing sites 66 may be at, adjacent, or near one or more stimulation sites 64, or remote from one or more of stimulation sites 64. For example, a sensing site 66a may be adjacent stimulation sites 64a, 64b, and 64c. A sensing site 66c may be relatively remote from stimulation sites 64a, 64b, and 64c. The terms "remote" and "adjacent" are indicate relative proximity. For example, locations or sites that are remote from each other may be separated by at greater than about 10 mm, or greater than about 100 mm. Locations or sites that are adjacent each other may be separated by a distance of less than about 10 mm, or less than about 1 mm. In some examples, the terms "remote" and "adjacent" may vary with the level of stimulation metric level or level of EMG responses. For example, sites that are "remote" for a relatively lower stimulation metric level may be "adjacent" at relatively higher stimulation metric level. In some examples, a "remote" location may refer to a site at which substantially no effect of an applied stimulation is intended, while an "adjacent" location may refer to a site at which at least some effect of an applied stimulation is intended.

As one or both of stimulation lead 18 and sensing lead 20 are moved, stimulation electrode 16 and sensing electrode 22 may move to or along different stimulation and sensing sites. In some examples, a movement of stimulation lead 18 may result in respective stimulation electrodes occupying respective stimulation sites, for example, stimulation electrode 60*b* at stimulation site 64*c*. In some examples, a movement of sensing lead 20 may result in respective sensing electrodes occupying respective sensing sites, for example, sensing electrode 62*b* at sensing site 66*b*.

While in some examples, stimulation lead 18 and sensing lead 20 may be moved to stimulate or sense activity at different sites, in some examples, stimulation or sensing may be performed at different sites, without moving either of stimulation lead 18 or sensing lead 20. For example, one of stimulation lead 18 or sensing lead 20 may be disposed in a fixed configuration, while the other of stimulation lead 18 or sensing lead 20 may be moved. In some examples, both stimulation lead 18 and sensing lead 20 may be disposed in a fixed configuration. For example, stimulation lead 18 may include more than one stimulation electrodes 60, for example, 60*a*-60*d*, sensing lead 20 may include more than one sensing electrodes 62, for example, 62*a*-62*d*, and one or both of stimulation lead 18 or sensing lead 20 may be disposed in a fixed configuration. For example, each of sensing electrodes 62*a*-62*d* may be maintained at a fixed relative distance from respective ones of stimulation electrodes 60*a*-60*d*. Medical device 30 may generate a stimulation signal for delivery through one or more of stimulation electrodes 60*a*-60*d*, and may receive a signal indicative of EMG responses sensed by one or more of sensing electrodes 62*a*-62*d*. In some examples, more than one stimulation lead 18 or more than one sensing lead 20 may be used. Thus, stimulation may be delivered, and EMG responses to the stimulation may be monitored, at multiple sites, without moving stimulation lead 18 or sensing lead 20.

In some examples, medical device 30 may control placement of, and stimulation and sensing through, stimulation lead 18 or sensing lead 20, in an automated or semi-automated manner, as described with reference to example techniques described elsewhere in the disclosure. In some examples, medical device 30 may guide a clinician on placing one or both of stimulation lead 18 or sensing lead 20, for example, by providing real-time or near real-time feedback to the clinician based on sensed EMG responses of the electrical stimulation that is delivered.

In some examples, medical device 30 may be used for a multi-stage placement of stimulation lead 18 or sensing lead 20, for example, a coarse placement and a fine placement. For example, a first coarse tuning may be performed to determine a general region for placement of stimulation lead 18 or sensing lead 20. After the coarse tuning, suitable locations or placement of stimulation lead 18 or sensing lead 20 within the general region may be determined by fine tuning, for example, by moving or changing locations or orientations of stimulation lead 18 or sensing lead 20 only by relatively small displacements.

Thus, in some examples, medical device 30 may be configured to control at least one stimulation electrode 16 to deliver electrical stimulation at a plurality of different stimulation metric levels at each of a plurality of different positions or at stimulation sites 64 within a tissue of patient 12. The stimulation metric levels may include stimulation intensity or amplitude, stimulation frequency, pulse width, or the like, or some combination thereof. While example systems and techniques are described with reference to stimulation intensity levels, example systems and techniques according to the disclosure may also be implemented to account for different stimulation metric levels, for example, frequency or pulse width, in addition to, or instead of, stimulation intensity. In some examples, medical device 30 may be configured to sense electromyographic (EMG) responses of the tissue of patient 12 to the electrical stimulation delivered at each of the different positions or at stimulation sites 64 and at each of the different intensity levels. Medical device 30 may select, or a clinician may select, based on feedback or guidance provided by medical device 30, one or more of the positions for chronic implantation of at least one implantable electrode. In some examples, the selection may be based on at least one stimulation intensity level sufficient to evoke a sensed EMG response of the sensed EMG responses in response to the delivery of the electrical stimulation at a respective position of the one or more positions, and a level of the sensed EMG response produced in response to the delivery of the electrical stimulation at the at least one stimulation metric level of the plurality of stimulation metric levels at the respective position.

In some examples, medical device 30 may score one or more of the positions for chronic implantation of at least one implantable electrode based on (a) at least one stimulation intensity level sufficient to evoke a sensed EMG response of the sensed EMG responses in response to the delivery of the electrical stimulation at a respective position of the one or more positions, and (b) a level of the sensed EMG response produced in response to the delivery of the electrical stimulation at the at least one stimulation metric level of the plurality of stimulation metric levels at the respective position. For example, medical device 30 may assign an alphanumeric label, an alphabetical label, a numeric label, or a numeric score or ranking to one or more of the positions. Generally, medical device 30 may score a plurality of positions, which may be all of the positions tested. In some examples, medical device 30 may rank the positions. For example, medical device 30 may rank positions based on the proximity of stimulation metric levels associated with the positions to the predetermined metric threshold. For example, positions associated with stimulation metric levels closest to the predetermined metric threshold may be ranked higher (e.g., a higher ranking indicates a position with a better fit for therapy). In some examples, one or more positions of the different positions may be selected for chronic implantation of an electrode based on the score. In some examples, medical device 30 or a clinician may be presented, via a user interface, the scores for the possible positions. Then, medical device 30 may receive a user selection of a desired position, which may be the position having a highest rank or highest score.

Figure 4A:
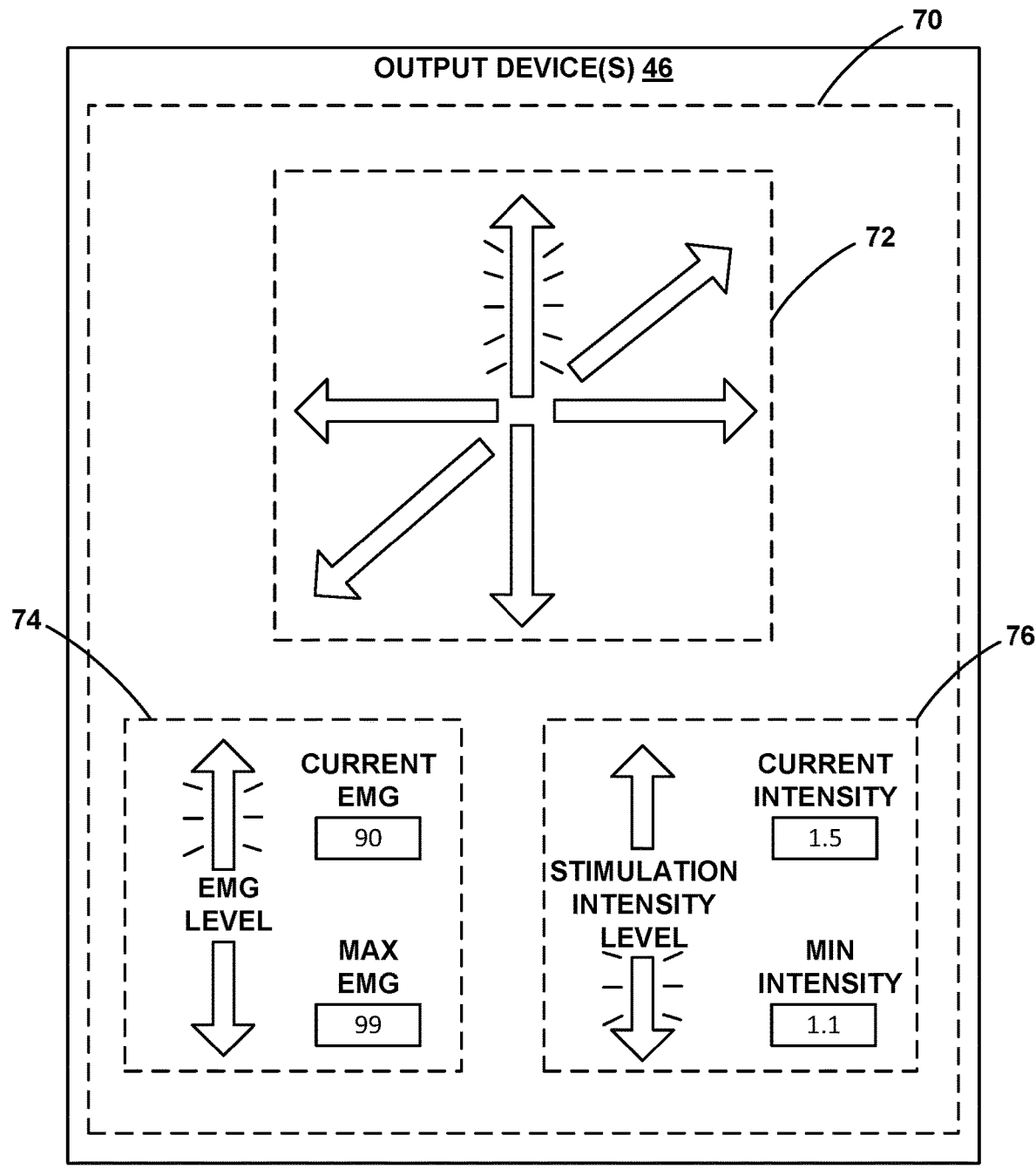
FIG. 4A is a conceptual and schematic diagram illustrating an example graphical output displayed by an example output device of a medical device coupled to a stimulation electrode and a sensing electrode.

FIG. 4A is a conceptual and schematic diagram illustrating an example graphical output 70 displayed by output device 46 of medical device 30 coupled to stimulation electrode 16 and sensing electrode 22. In some examples, medical device 30 may indicate a state of electrode placement, or may guide a clinician on electrode placement, via feedback provided on output device 46. Graphical output 70 may include one or more graphical elements indicative of one or more of a stimulation metric level, EMG response, scores, rankings, or suggested movement or placement of electrodes. For example, as shown in FIG. 4A, graphical output 70 may include a navigation panel 72, an EMG panel 74, and a stimulation panel 76. Navigation panel 72 may indicate a suggested direction of movement of stimulation lead 18 to result in movement of stimulation electrode 16, or movement of sensing lead 20 to result in movement of sensing electrode 22, towards a predetermined site. For example, as shown in FIG. 4A, a flashing up arrow may be indicative of a suggested upward movement of an electrode. EMG panel 74 may indicate whether EMG responses are increasing or decreasing in intensity as an electrode is moved along a direction. For example, a flashing upward arrow, as shown in FIG. 4A, may indicate an increase in EMG response intensity. EMG panel 74 may also indicate a current magnitude or level of EMG response sensed by a particular sensing electrode 22, or a time-averaged EMG response over a predetermined window of time, or an electrode-averaged EMG response for more than one electrode at a particular interval of time. In some examples, EMG panel 74 may also indicate a maximum magnitude or level of EMG responses, for example, a maximum response over a predetermined window of time, or a maximum response sensed by a particular electrode compared to responses sensed by other electrodes.

Stimulation panel 76 may indicate whether stimulation intensities are increasing or reducing in intensity, for example, in response to a control signal sent by medical device 30, or by the clinician. For example, a flashing downward arrow, as shown in FIG. 4A, may indicate a reduction in stimulation responses. Stimulation panel 76 may also indicate a current magnitude or level of stimulation intensity delivered by a particular stimulation electrode 16, or a time-averaged stimulation intensity over a predetermined window of time, or an electrode-averaged stimulation intensity for more than one electrode at a particular interval of time. In some examples, stimulation panel 76 may also indicate a metric threshold, a minimum magnitude, or level of stimulation intensity or another stimulation metric level that resulted in an EMG response above a predetermined threshold, for example, a minimum stimulation intensity over a predetermined window of time, or a minimum stimulation intensity delivered by a particular electrode compared to stimulation intensities delivered by other electrodes.

In some examples, a stimulation metric level (e.g., stimulation intensity, frequency, pulse width, or the like, or any combination thereof) that is relatively low, but sufficient to evoke an EMG response may help locate suitable placement for implantation of electrodes in the patient. An EMG response may be determined to be evoked with reference to a baseline EMG, for example, an EMG prior to delivering any stimulation. In some examples, an EMG response having a parameter higher than a predetermined threshold may be considered to be a EMG response evoked by the stimulation. For example, an EMG response having a root mean square (RMS) power higher than a predetermined RMS power may be an EMG response evoked by the stimulation. In some examples, an EMG response associated with an area under a curve (AUC) of an EMG signal greater than a predetermined threshold AUC may be an EMG response evoked by the stimulation. In some examples, an EMG response having an RMS power, an AUC, or another EMG metric sufficiently large for a therapeutic outcome may be an EMG response evoked by the stimulation.

In some examples, patient or clinician input may be used to determine whether an EMG response is evoked by the stimulation. In some examples, a patient may indicate a sensory or motor response associated with EMG, which may be indicative of an EMG response evoked by the stimulation. In some examples, a clinician may observe a change in an EMG signal indicative of a stimulation metric level sufficient to evoke an above-threshold EMG response. For example, a clinician may monitor one or more EMG parameters such as EMG amplitude or pulse-width, and observe for discernable fluctuations or inflection in magnitude of the EMG parameters indicative of an EMG response evoked by the stimulation.

Figure 4B:
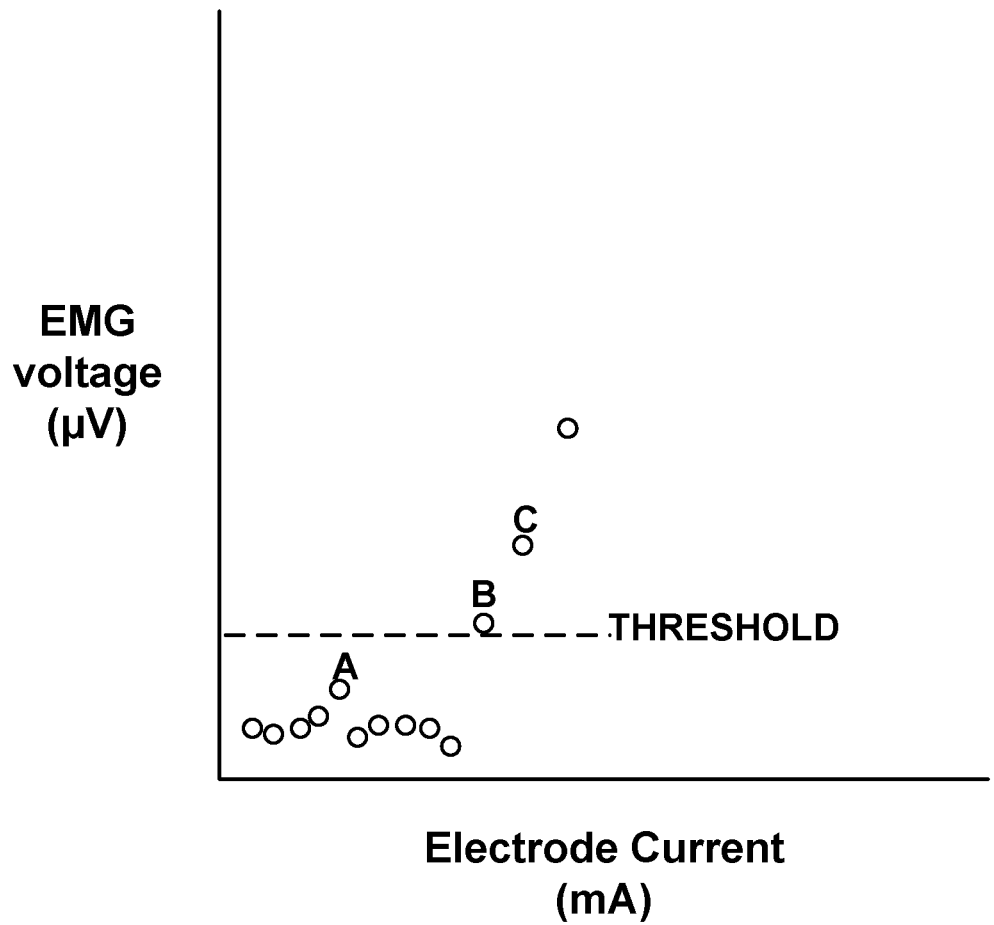
FIG. 4B is a graph illustrating an example plot indicating magnitudes of sensed EMG responses.

FIG. 4B is a graph illustrating an example plot indicating magnitudes of sensed EMG responses. The plot indicates sensed EMG voltage versus electrode current. EMG responses lower than a threshold (e.g., the dotted line between points "A" and "B") may be considered as background signals, noise, or statistical fluctuations, and may not be considered to be an EMG response to a stimulus. For example, while point "A" may be associated with a relatively higher EMG voltage, it may be below the threshold. Point "B" may mark an inflection point in the curve, for example, determined by a clinician or a processor. In some examples, the threshold may be set to be close to the inflection point, for example, just lower than the inflection point. In some examples, while an EMG response may be considered to be evoked in response to a stimulus when the EMG response is supra-threshold, such an EMG response may not be sensed by a patient. For example, a patient may not sense EMG response "B" because the response is below the perception threshold for the patient, even though response "B" may be above a motor threshold or EMG response threshold from a sufficient stimulation metric level. In some examples, where a threshold may or not be set, any EMG response that may be sensed by a patient may be considered to be a EMG response supra-threshold to indicate a response to stimulus. For example, EMG response "C" may be a response that may be sensed by a patient (e.g., above perception threshold). In some examples, the threshold may be set close to a response sensed by a patient.

While FIG. 4B is described with reference to EMG voltage and stimulation current, any suitable EMG characteristic and stimulation parameter may be used instead of, or in addition to EMG voltage, to determine if an EMG signal is a response to a stimulus. For example, magnitudes of any suitable EMG parameters such as RMS power, AUC, intensity, or any other suitable EMG parameter may be used to determine if an EMG signal is indicative of a response, or instead noise, statistical fluctuation, or a non-stimulus responsive EMG signal.

In some examples, medical device 30 may be configured to sense the EMG responses by receiving at least one signal from at least one sensing electrode 22 that is indicative of the sensed EMG responses. Medical device 30 may score, for example, based on the sensed EMG responses, one or more of the probe positions for chronic implantation of at least one implantable electrode (not shown). In some examples, medical device 30 or a clinician may select one or more of the probe positions for chronic implantation, based on respective scores associated with the respective positions. Thus, in some examples, system 10 may include at least one implantable electrode configured to deliver electrical stimulation. In some examples, the construction of at least implantable electrode may be substantially similar to that of at least one stimulation electrode 16. In some examples, the at least one implantable electrode may include at least one stimulation electrode 16. In some examples, the at least one implantable electrode may consist of at least one stimulation electrode 16. For example, the same at least stimulation electrode 16 used to determine or guide electrode placement, may be implanted chronically as at least one implantable electrode.

Figure 5:
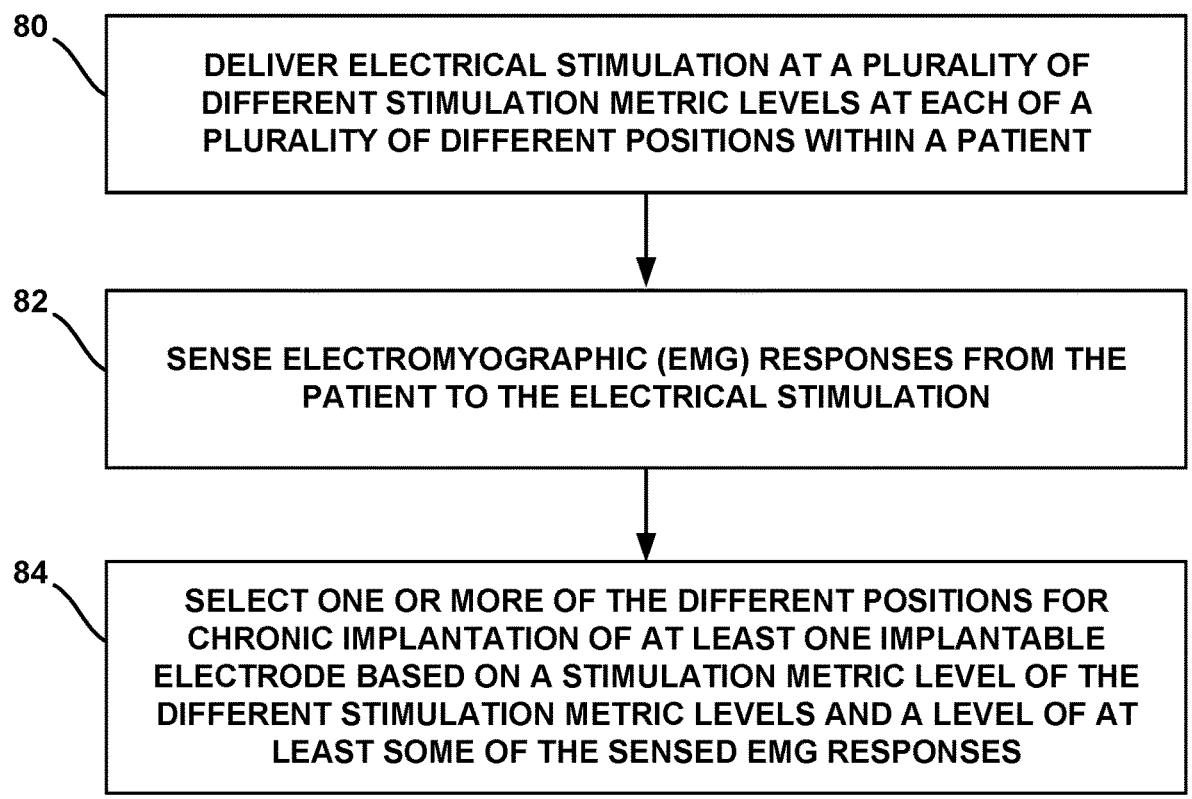
FIG. 5 is a flow diagram illustrating an example technique for determining a chronic implantation site of a stimulation electrode within a tissue.

FIG. 5 is a flow diagram illustrating an example technique for determining a chronic implantation site of a stimulation electrode within a tissue. The example technique of FIG. 5 is described with reference to system 10 and medical device 30. However, the example technique may be implemented using any suitable system according to the disclosure. In some examples, processing circuitry 40 controls stimulation circuitry 57 to deliver electrical stimulation at a plurality of different stimulation metric levels at each of a plurality of different positions within a tissue of patient 12 (80). The different positions may be chosen randomly, semi-randomly, or deterministically, for example, to be uniformly or substantially uniformly distributed within a determined region of the patient. In some examples, the different positions may be clustered about a predetermined target site. For example, a clinician may position stimulation lead 18 to place at least one stimulation electrode 16 at each of the plurality of different positions. In some examples, the clinician may move one electrode of the at least one stimulation electrode 16 to the different positions. In other examples, the clinician may move multiple electrodes of the at least one stimulation electrode 16 to the different positions. Medical device 30 may deliver electrical stimulation via stimulation circuitry 57 through the at least one stimulation electrodes 16 to the different positions. In some examples, medical device 30 may control at least one placement controller 58 to move and place at least one stimulation electrode 16 in one or more positions of the different positions and may control stimulation circuitry 57 to deliver the electrical stimulation at the different positions. In some examples, medical device 30 and the clinician may move and place at least one stimulation electrode 16. For example, medical device 30 may control an initial positioning, while the clinician may reposition or finalize the position of at least one stimulation electrode 16.

Medical device 30 may deliver different stimulation levels at different positions by delivering stimulation via different stimulation electrodes 16 along the same stimulation lead 18, or by delivering stimulation via different stimulation electrodes along different stimulation leads 18, or by moving stimulation lead 18 to change a position of stimulation electrode 16 (80). For example, processing circuitry 40 may send a control signal to control stimulation circuitry 57 to apply a predetermined level of stimulation current or voltage to at least one stimulation electrode 16, based on control instructions 54. While medical device 30 may deliver stimulation via stimulation circuitry according to control instructions 54, in some examples, the clinician may augment or modify control instructions 54 to change the intensity or another stimulation metric level of stimulation.

The example technique includes, by medical device 30, sensing electromyographic (EMG) responses of the tissue of patient 12 to the electrical stimulation delivered (82). For example, processing circuitry 40 of medical device 30 may control sensing circuitry 56 to receive a signal from sensing electrode 22 that is indicative of the sensed EMG responses and the respective position or site at which a respective EMG response was sensed. In some examples, sensing the EMG responses (82) may include, by processing circuitry 40, one or both of sensing the EMG responses of the tissue of patient 12 adjacent the respective position or sensing the EMG responses of the tissue of the patient remote from the respective position, for example, as described with reference to FIG. 3. In some examples, sensing the EMG responses includes, by processing circuitry 40, sensing the EMG responses of the tissue of the patient adjacent the respective position. In some examples, sensing the EMG responses includes, by processing circuitry 40, sensing the EMG responses of the tissue of the patient remote from the respective position. For example, processing circuitry 40 may receive signals indicative of EMG responses and analyze the signals based on signal processing instructions 50 to determine the EMG responses, or otherwise sense EMG responses, by activating or receiving signals through different sensing electrodes 22 along the same sensing lead 20, or via sensing electrodes along different sensing leads 20. In some examples, processing circuitry may move sensing lead 20 to change a position of sensing electrode 22, for example, by sending a control signal to at least one placement controller 58 to control at least one placement motor 59 to move sensing lead 20 or sensing electrode 22.

The example technique may also include, by medical device 30, selecting one or more of the positions for chronic implantation of at least one implantable electrode (84). For example, processing circuitry 40 of medical device 30 may select or indicate the suitability of one or more positions for chronic implantation based on a at least one stimulation intensity level (for example, greater than a predetermined stimulation metric threshold) sufficient to evoke a sensed EMG response of the sensed EMG responses in response to the delivery of the electrical stimulation, and a level of the sensed EMG response produced in response to the delivery of the electrical stimulation at the at least one stimulation metric level at the respective position.

Processing circuitry 40 may analyze an EMG response differently based on signal processing instructions 50 depending on whether the EMG response is associated with a location adjacent to a stimulation location or whether the EMG response is associated with a location remote from the stimulation location. In some examples, processing circuitry 40 may select the one or more of the positions (84) by selecting at least one position of the positions associated with a maximum sensed EMG response of the respective EMG responses adjacent the respective position. In some examples, processing circuitry 40 may select the one or more of the positions (84) by selecting at least one position of the positions associated with a minimum sensed EMG response of the respective EMG responses remote from the respective position. For example, a relatively high EMG response, or an EMG response greater than a predetermined upper threshold, or a maximum EMG response, may be sought adjacent a stimulation site. A relatively low EMG response, or an EMG response lower than a lower predetermined threshold, or a minimum EMG response, or substantially no EMG response, may be sought remote from a stimulation site, for example, to avoid side effects associated with stimulating unintended sites remote from an intended stimulation site.

Medical device 30 may output a feedback signal indicative of the selected position via output device 46. For example, processing circuitry 40 may send a control signal to output device 46 to drive an output of output device 46 that provides feedback to a clinician while the clinician moves at least one electrode. In some examples, processing circuitry 40 may send a control signal to output device 46 to drive an output of output device 46 that provides real time or near real time status of electrode placement, for example, when medical device 30 is performing automated or semi-automated electrode placement.

In some examples, the selecting (84) may further include correlating respective EMG responses with sensory feedback received from patient 12. For example, patient 12 may indicate increasing or decreasing discomfort, pain, sensation, throbbing, tremor, or feeling, as an electrode is moved, or as a stimulation metric level (for example, intensity) is changed. A clinician or medical device 30 may account for both the patient feedback and feedback provided by medical device 30 in placing electrodes and controlling stimulation metric levels. In some examples, patient 12 may provide verbal, visual, or tactile feedback to the clinician. In other examples, patient 12 may activate or operate a patient controller to send a control signal to processing circuitry 40 that may be indicative of the patient feedback.

After processing circuitry 40 selects one or more of the different positions for chronic implantation (84), processing circuitry 40 may control stimulation circuitry 57 to deliver electrical stimulation therapy via the at least implantable electrode, for example, at least one stimulation electrode 16, at the at least one stimulation metric level sufficient to evoke EMG responses at the selected position of the one or more positions. Thus, according to these and other examples herein, medical device 30 may control the placement of, or guide a clinician on the placement of, electrodes for stimulating a stimulation target to treat a patient condition or disorder.

EXAMPLES

Example 1

Figure 6:
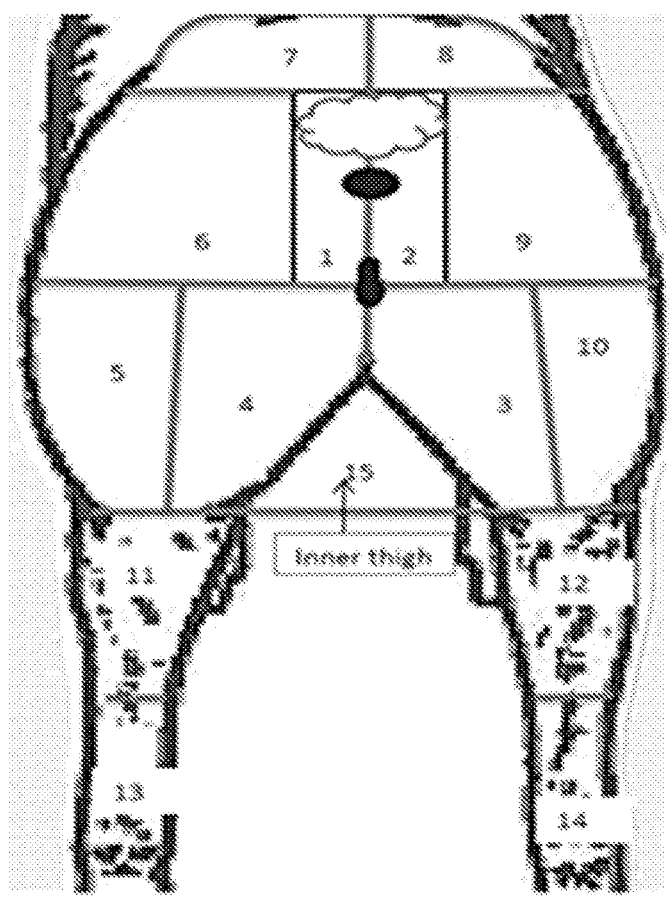
FIG. 6 is a schematic diagram illustrating example candidate tissue zones for implanting stimulating electrodes in a test sheep.
Figure 7:
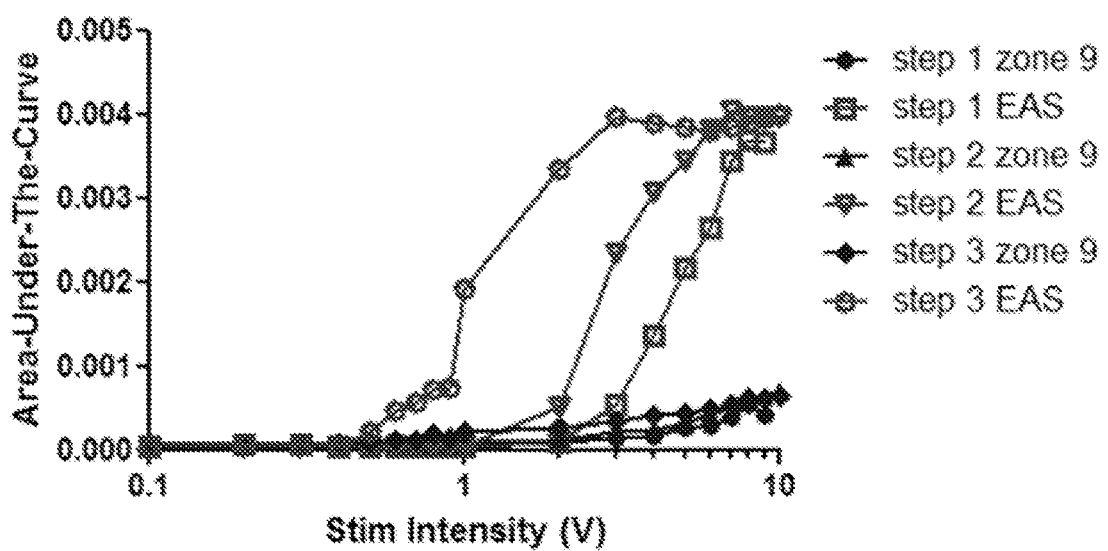
FIG. 7 is a chart illustrating a variation in example EMG signals in response to electrode targeting by disposing electrodes within different tissue zones in sheep with different stimulation intensities.

Stimulation studies were conducted on sheep. Stimulation response data was collected in a sheep study at using InterStim® leads (Model 3889, Medtronic, Inc., Minneapolis, MN). FIG. 6 is a schematic diagram illustrating example candidate tissue zones for implanting stimulating electrodes in test sheep. In the sheep, InterStim® leads were implanted in the S3 foramina at different positions. EMG responses were recorded from zone 9, shown in FIG. 6, and from the external anal sphincter (EAS), using Enterra® leads (Medtronic, Inc., Minneapolis, Minn). FIG. 7 is a chart illustrating a variation in example EMG signals (area under the curve, AUC, in mV-sec) in response to electrode targeting by disposing electrodes within different tissue zones in sheep with different stimulation intensities. At a position 1, the EMG evoked by sacral neuromodulation was reported as motor threshold and responses to increased stimulation intensity (stronger signals at anal sphincter and weaker signals at pelvic floor). When the electrode moved to a position 2, the response threshold dropped and response increased. When the electrode moved to a position 3, the lowest response threshold and strongest response to sacral nerve stimulation were obtained. Position 3 was closest to the nerve target, while position 1 was farthest from the nerve target. The electrode was fixed at the position 3 and implanted permanently.

Example 2

Figure 8:
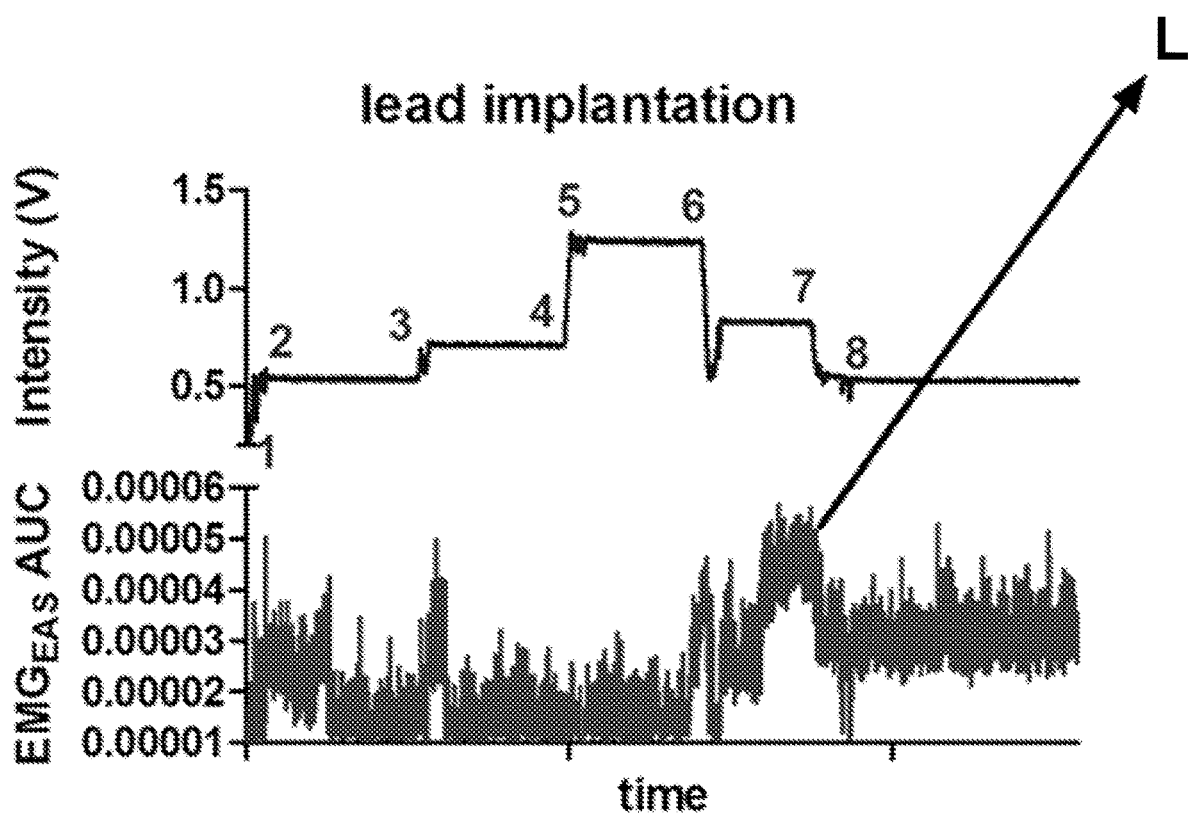
FIG. 8 is a chart illustrating a variation in example EMG signals in response to different stimulation electrode configurations and stimulation intensities.

The effect of changing stimulation intensity and electrode position on evoked EMGs was evaluated. FIG. 8 is a chart illustrating a variation in example EMG signals (area under the curve, AUC, mV-sec) in response to different electrode configurations and stimulation intensities. A test electrode was placed at an initial position (1). No stimulation evoked EMGs were observed. The stimulation intensity was increased until EMGs were observed (2). The intensity was maintained at that first intensity level, and the electrode was moved along a first test direction. As the electrode was moved along the first direction, the EMGs diminished and ended. The intensity was increased from the first intensity level to a second intensity level at which EMGs were observed again (3). The intensity was maintained at that second intensity level, and the electrode was moved along a second test direction. As the electrode was moved along the first direction, the EMGs diminished and ended (4). The stimulation intensity was further increased from the second intensity level to a third intensity level (5), however, no EMGs were observed. The electrode was moved along a third test direction. The EMGs were again observed. The stimulation intensity was reduced from the third intensity level to a fourth intensity level that still resulted in EMGs (7). The electrode was moved again until the EMGs continued to exhibit an increase (7). The location 'L' corresponding to the maximum EMG and lowest $T_{mot}$ (motor threshold intensity) was identified for final electrode placement.

Example 3

Figure 9:
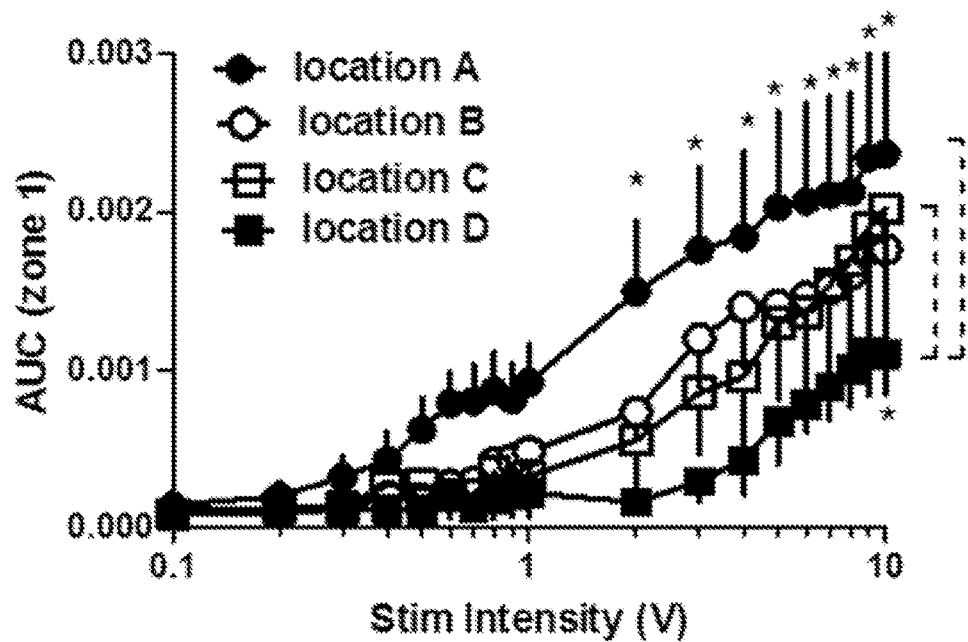
FIG. 9 is a chart illustrating a variation in example EMG signals in different locations within a single tissue zone at different stimulation intensities.

The effect of changing stimulation intensity and electrode position EMGs evoked by spinal nerve stimulation was evaluated. FIG. 9 is a chart illustrating a variation in example EMG signals (area under the curve, AUC) in different locations within a single tissue zone at different stimulation intensities. EMG AUC (in mV-sec) was sensed in zone 1 in response to four lead locations in six implantation trials. Location A was found to be optimal while, strongest EMG response was evoked at the optimal area zone.

Figure 10:
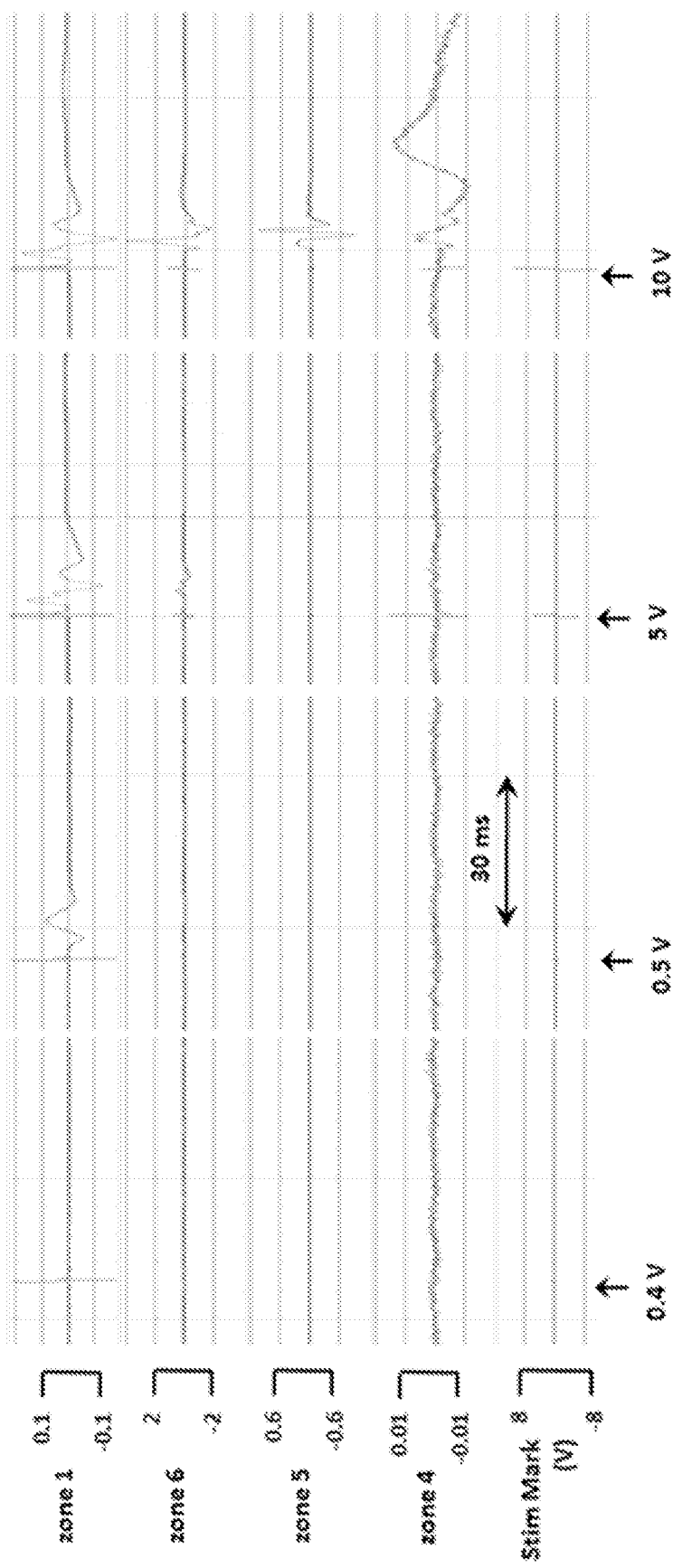
FIG. 10 is a chart illustrating a variation in example EMG signals in different tissue zones and for different stimulation intensities.

FIG. 10 is a chart illustrating a variation in example EMG signals (mV) in different tissue zones and for different stimulation intensities. EMG (mV) responses from different myotome zones to different intensities of spinal nerve stimulation (3−/0+, 10 Hz, pulse width 0.21 ms) were sensed in anesthetized condition. The spinal nerve stimulation (Stim Mark) is shown at the bottom panel of FIG. 10. The EMG responses from zone 1 to electrical stimulation appeared at a stimulation level of 0.5 V. Stimulation at 5 V evoked EMG response at zone 6, and stimulation at 10 V evoked strongest EMG waveforms from all the channels.

FIGS. 11A-11D are charts illustrating examples variations in EMG signals sensed at different zones and locations with different stimulation intensities. The summary data for stimulus-response functions of EMG activities (area under the curve, AUC, mV-sec) from different myotome zones to graded intensity of stimulation at different lead locations is presented in FIGS. 11A-11D. Lead location (A) was found to trigger a strong response from zone 1. Lead location (D) was found to be the worst with a stronger EMG response from zone 6. Therefore, chronic implantable electrodes would be positioned in zone 1 in Example 3 due to the sensed EMG responses to different stimulation intensity levels as measured.

Example 1: A system comprising: a stimulation circuitry configured to generate electrical stimulation deliverable to a patient; sensing circuitry configured to sense electromyographic (EMG) responses from the patient; and processing circuitry configured to: control the stimulation circuitry to deliver, via at least one electrode, the electrical stimulation at a plurality of different stimulation metric levels at each of a plurality of different positions within the patient; sense, via the sensing circuitry, electromyographic (EMG) responses from the patient to the electrical stimulation, and score one or more of the different positions for chronic implantation of at least one implantable electrode based on: at least one stimulation metric level of the plurality of different stimulation metric levels greater than a predetermined metric threshold sufficient to evoke at least some of the sensed EMG responses to the delivery of the electrical stimulation at a respective position of the one or more positions, and a level of the at least some of the sensed EMG responses produced in response to the delivery of the electrical stimulation at the at least one stimulation metric level at the respective position.

Example 2: The system of example 1, wherein the processing circuitry is configured to select one or more of the different positions for chronic implantation of at least one implantable electrode based on respective scores associated with respective positions of the different positions.

Example 3: The system of example 1 or 2, further comprising the at least one implantable electrode, wherein the processing circuitry is configured to control the stimulation circuitry to deliver electrical stimulation therapy via the at least implantable electrode at the at least one stimulation metric level at the selected position of the one or more positions.

Example 4: The system of any of examples 1 to 3, further comprising at least one placement motor, and wherein the processing circuitry is configured to control the placement motor to move the at least one electrode in response to the sensed EMG responses.

Example 5: The system of example 4, wherein the processing circuitry is configured to control the placement motor to move the at least one electrode toward the selected position of the one or more positions.

Example 6: The system of any of examples 1 to 5, wherein the stimulation metric comprises one of a stimulation pulse width, a stimulation intensity, or a stimulation frequency.

Example 7: The system of any of examples 1 to 6, further comprising: a medical device comprising the processing circuitry, the stimulation circuitry, and the sensing circuitry; and the at least one electrode configured to be coupled to the medical device.

Example 8: The system of example 7, wherein the at least one electrode comprises the at least one implantable electrode.

Example 9: The system of example 7, wherein the processing circuitry is configured to sense the EMG responses by receiving at least one signal from the at least one electrode and via the sensing circuitry indicative of tissue response evoked by the delivered electrical stimulation.

Example 10: The system of any of examples 1 to 9, wherein the at least one electrode comprises one or more of an implanted electrode, an external patch electrode, or a needle electrode.

Example 11: The system of any of examples 1 to 10, wherein the at least one electrode comprises at least one of a local sensing electrode substantially adjacent the respective position of the different positions or at least one remote sensing electrode substantially remote from the respective position of the different positions.

Example 12: The system of any of examples 1 to 11, further comprising: a position detector device configured to generate a signal indicative of a position of the at least one electrode; and an output device, wherein the processing circuitry is configured to control the output device to output a feedback signal based on the signal received from the position detector device to guide a clinician as the at least one electrode is moved on a movable lead or located along an axial length of a fixed lead.

Example 13: The system of example 12, wherein the feedback signal comprises one or more of an electronic signal, a visual signal, an audible signal, or a haptic signal.

Example 14: The system of examples 12 or 13, wherein the output device comprises a fluoroscopic display configured to indicate respective positions, and wherein the output device is configured to present scores of one or more of the at least one electrode or the at least one implantable electrode and the respective EMG responses associated with the at least one electrode or the at least one implantable electrode.

Example 15: A method for positioning at least one electrode, the method comprising: delivering electrical stimulation at a plurality of stimulation metric levels at each of a plurality of different positions within a patient; sensing electromyographic (EMG) responses from the patient to the electrical stimulation; and scoring one or more of the different positions for chronic implantation of at least one implantable electrode based on: at least one stimulation metric level of the plurality of different stimulation metric levels greater than a predetermined metric threshold sufficient to evoke at least some of the sensed EMG responses to the delivery of the electrical stimulation at a respective position of the one or more different positions, and a level of the at least some of the sensed EMG responses produced in response to the delivery of the electrical stimulation at the at least one stimulation metric level at the respective position.

Example 16: The method of example 15, further comprising selecting one or more of the different positions for chronic implantation of at least one implantable electrode based on respective scores associated with respective positions of the different positions.

Example 17: The method of example 16, wherein selecting the one or more of the different positions comprises selecting at least one position of the different positions associated with a maximum sensed EMG response of the respective EMG responses.

Example 18: The method of example 16, wherein selecting the one or more of the positions comprises selecting at least one position of the different positions associated with a minimum sensed EMG response of the respective EMG responses.

Example 19: The method of any of examples 16 to 18, wherein the selecting further comprises correlating the respective EMG responses with sensory feedback received from the patient.

Example 20: The method of any of examples 16 to 19, further comprising controlling the stimulation circuitry to deliver electrical stimulation therapy via the at least implantable electrode at the at least one stimulation metric level at the selected position of the one or more positions.

Example 21: The method of any of examples 15 to 20, wherein the stimulation metric comprises one of a stimulation pulse width, a stimulation intensity, or a stimulation frequency.

Example 22: The method of any of examples 15 to 21, wherein sensing the EMG responses comprises one or both of sensing the EMG responses from the patient adjacent the respective position of the different positions or sensing the EMG responses from the patient remote from the respective position of the different positions.

Example 23: The method of example 22, wherein sensing the EMG responses comprises sensing the EMG responses from the patient adjacent the respective position of the different positions.

Example 24: The method of example 22, wherein sensing the EMG responses comprises sensing the EMG responses from the patient remote from the respective position.

Example 25: The method of any of examples 15 to 24, wherein the level of the sensed EMG is lower than a predetermined upper threshold.

Example 26: The method of any of examples 15 to 25, wherein the level of the sensed EMG response is greater than a predetermined lower threshold.

Example 27: The method of any of examples 15 to 26, further comprising outputting a feedback signal configured to guide a clinician on one or both of moving the at least one electrode on a movable lead or locating the at least one electrode along an axial length of a fixed lead.

Example 28: The method of example 27, wherein the feedback signal comprises one or more of an electronic signal, a visual signal, an audible signal, or a haptic signal.

Example 29: The method of any of examples 15 to 28, wherein the one or more positions are within a pelvic floor region of the patient.

Example 30: A non-transitory computer readable storage medium comprising instructions that, when executed, cause processing circuitry to: deliver electrical stimulation at a plurality of different stimulation metric levels at each of a plurality of different positions a patient; sense electromyographic (EMG) responses from the patient to the electrical stimulation; and score one or more of the different positions for chronic implantation of at least one implantable electrode based on: at least one stimulation metric level of the plurality of different stimulation metric levels greater than a predetermined metric threshold sufficient to evoke at least some of the sensed EMG responses to the delivery of the electrical stimulation at a respective position of the one or more positions, and a level of the at least some of the sensed EMG responses produced in response to the delivery of the electrical stimulation at the at least one stimulation metric level at the respective position.

Example 31: The non-transitory computer readable storage medium of example 30, further comprising instructions that, when executed, cause the processing circuitry to select one or more of the different positions for chronic implantation of at least one implantable electrode based on respective scores associated with respective positions of the different positions.

Example 32: The non-transitory computer readable storage medium of example 31, further comprising instructions that, when executed, cause the processing circuitry to control the at least one implantable electrode to deliver electrical stimulation therapy at the at least one stimulation metric level at the selected position of the one or more positions.

Example 33: The non-transitory computer readable storage medium of example 31 or 32, further comprising instructions that, when executed, cause the processing circuitry to control the placement motor to move the at least one electrode toward the selected position of the one or more positions.

Example 34: The non-transitory computer readable storage medium of any of examples 30 to 33, wherein the stimulation metric comprises a stimulation pulse width, a stimulation intensity, or a stimulation frequency.

Example 35: The non-transitory computer readable storage medium of any of examples 30 to 34, further comprising instructions that, when executed, cause the processing circuitry to sense EMG responses by receiving at least one signal from the at least electrode indicative of the tissue response evoked by the delivered electrical stimulation.

Example 36: The non-transitory computer readable storage medium of any one of examples 30 to 35, further comprising instructions that, when executed, cause the processing circuitry to one or both of sense the EMG responses from the patient adjacent the respective position of the different positions or remote from the respective position of the different positions.

Example 37: The non-transitory computer readable storage medium of any of examples 30 to 36, further comprising instructions that, when executed, cause the processing circuitry to: detect a position of the at least one electrode; and based on the position of the at least one electrode, output a feedback signal configured to guide a clinician on one or both of moving the at least one electrode on a movable lead or locating the at least one electrode along an axial length of a fixed lead.

Example 38: The non-transitory computer readable storage medium of example 37, wherein the feedback signal comprises one or more of an electronic signal, a visual signal, an audible signal, or a haptic signal.

Example 39: The non-transitory computer readable storage medium of any of examples 30 to 39, further comprising instructions that, when executed, cause the processing circuitry to control a placement motor to move the at least one electrode in response to the sensed EMG responses.

The techniques described in this disclosure may be implemented, at least in part, in hardware, software, firmware, or any combination thereof. For example, various aspects of the described techniques may be implemented within processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described instructions, units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the processing circuitry. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In some examples, an article of manufacture may comprise one or more computer system-readable storage media.

Various examples have been described. These and other examples are within the scope of the following claims.

What is claimed is:

1. A system comprising:
stimulation circuitry configured to generate electrical stimulation deliverable to a patient;
sensing circuitry configured to sense electromyographic (EMG) responses from the patient; and
processing circuitry configured to:
control the stimulation circuitry to deliver, via at least one electrode, the electrical stimulation at a plurality of different stimulation metric levels at each of a plurality of different positions within the patient;
sense, via the sensing circuitry, electromyographic (EMG) responses from the patient to the electrical stimulation,
score the different positions for chronic implantation of at least one implantable electrode based on:
at least one stimulation metric level of the plurality of different stimulation metric levels greater than a predetermined metric threshold, the predetermined metric threshold being sufficient to evoke at least some of the sensed EMG responses to the delivery of the electrical stimulation at a respective position of the plurality of different positions, and
a level of the at least some of the sensed EMG responses produced in response to the delivery of the electrical stimulation at the at least one stimulation metric level at the respective position; and
select one position of the plurality of different positions for delivery of electrical stimulation therapy, the one position having a score higher than scores of other positions, and wherein higher scores comprise a stronger level of sensed EMG response than sensed EMG responses of lower scores.

2. The system of claim 1, wherein the processing circuitry is configured to select the one position for chronic implantation of at least one implantable electrode based on respective scores associated with respective positions of the different positions.

3. The system of claim 1, further comprising the at least one implantable electrode, wherein the processing circuitry is configured to control the stimulation circuitry to deliver the electrical stimulation therapy via the at least one implantable electrode at the at least one stimulation metric level at the selected one position of the one or more positions.

4. The system of claim 3, further comprising at least one placement motor, and wherein the processing circuitry is configured to control the placement motor to move the at least one electrode in response to the sensed EMG responses.

5. The system of claim 4, wherein the processing circuitry is configured to control the placement motor to move the at least one electrode toward the selected position of the one or more positions.

6. The system of claim 1, wherein the stimulation metric comprises one of a stimulation pulse width, a stimulation intensity, or a stimulation frequency.

7. The system of claim 1, further comprising:
a medical device comprising the processing circuitry, the stimulation circuitry, and the sensing circuitry; and
the at least one electrode configured to be coupled to the medical device.

8. The system of claim 7, wherein the at least one electrode comprises the at least one implantable electrode.

9. The system of claim 7, wherein the processing circuitry is configured to sense the EMG responses by receiving at least one signal from the at least one electrode and via the sensing circuitry indicative of tissue response evoked by the delivered electrical stimulation.

10. The system of claim 1, wherein the at least one electrode comprises one or more of an implanted electrode, an external patch electrode, or a needle electrode.

11. The system of claim 1, wherein the at least one electrode comprises at least one of a local sensing electrode substantially adjacent the respective position of the different positions or at least one remote sensing electrode substantially remote from the respective position of the different positions.

12. The system of claim 1, further comprising:
a position detector device configured to generate a signal indicative of a position of the at least one electrode; and
an output device, wherein the processing circuitry is configured to control the output device to output a feedback signal based on the signal received from the position detector device to guide a clinician as the at least one electrode is moved on a movable lead or located along an axial length of a fixed lead.

13. The system of claim 12, wherein the feedback signal comprises one or more of an electronic signal, a visual signal, an audible signal, or a haptic signal.

14. The system of claim 12, wherein the output device comprises a fluoroscopic display configured to indicate respective positions, and wherein the output device is configured to present scores of one or more of the at least one electrode or the at least one implantable electrode and the respective EMG responses associated with the at least one electrode or the at least one implantable electrode.

15. A method for positioning at least one electrode, the method comprising:
delivering electrical stimulation at a plurality of stimulation metric levels at each of a plurality of different positions within a patient;
sensing electromyographic (EMG) responses from the patient to the electrical stimulation;
scoring the different positions for chronic implantation of at least one implantable electrode based on:
at least one stimulation metric level of the plurality of different stimulation metric levels greater than a predetermined metric threshold, the predetermined metric threshold being sufficient to evoke at least some of the sensed EMG responses to the delivery of the electrical stimulation at a respective position of the plurality of different positions, and
a level of the at least some of the sensed EMG responses produced in response to the delivery of the electrical stimulation at the at least one stimulation metric level at the respective position; and
selecting one position of the plurality of different positions for delivery of electrical stimulation therapy, the one position having a score higher than scores of other positions, and wherein higher scores comprise a stronger level of sensed EMG response than sensed EMG responses of lower scores.

16. The method of claim 15, further comprising selecting the one position for chronic implantation of at least one implantable electrode based on respective scores associated with respective positions of the different positions.

17. The method of claim 16, wherein selecting the one position comprises selecting the one position of the different positions associated with a maximum sensed EMG response of the respective EMG responses.

18. The method of claim 15, wherein the selecting further comprises correlating the respective EMG responses with sensory feedback received from the patient.

19. The method of claim 15, further comprising controlling delivery of the electrical stimulation therapy via the at least one implantable electrode at the at least one stimulation metric level at the selected one position of the different positions.

20. A non-transitory computer readable storage medium comprising instructions that, when executed, cause processing circuitry to:
deliver electrical stimulation at a plurality of different stimulation metric levels at each of a plurality of different positions a patient;
sense electromyographic (EMG) responses from the patient to the electrical stimulation;
score the different positions for chronic implantation of at least one implantable electrode based on:
at least one stimulation metric level of the plurality of different stimulation metric levels greater than a predetermined metric threshold, the predetermined metric threshold being sufficient to evoke at least some of the sensed EMG responses to the delivery of the electrical stimulation at a respective position of the plurality of different positions, and
a level of the at least some of the sensed EMG responses produced in response to the delivery of the electrical stimulation at the at least one stimulation metric level at the respective position; and
select one position of the plurality of different positions for delivery of electrical stimulation therapy, the one position having a score higher than scores of other positions, and wherein higher scores comprise a stronger level of sensed EMG response than sensed EMG responses of lower scores.

\* \* \* \* \*